(12) United States Patent
MacMillan et al.

(10) Patent No.: US 7,323,604 B2
(45) Date of Patent: Jan. 29, 2008

(54) HYDRIDE REDUCTION OF α,β-UNSATURATED CARBONYL COMPOUNDS USING CHIRAL ORGANIC CATALYSTS

(75) Inventors: David MacMillan, Pasadena, CA (US);
Stephane Ouellet, St. Lazare, CA (US);
Jamison Tuttle, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 91 days.

(21) Appl. No.: 11/285,428

(22) Filed: Nov. 21, 2005

(65) Prior Publication Data

US 2006/0161024 A1 Jul. 20, 2006

Related U.S. Application Data

(60) Provisional application No. 60/642,700, filed on Jan. 10, 2005, provisional application No. 60/629,674, filed on Nov. 19, 2004.

(51) Int. Cl.
*C07C 45/00* (2006.01)
(52) U.S. Cl. .................. 568/312; 568/343; 568/458
(58) Field of Classification Search .................. None
See application file for complete search history.

(56) References Cited

U.S. PATENT DOCUMENTS

| | | | |
|---|---|---|---|
| 6,307,057 B1 | 10/2001 | MacMillan et al. | 548/316.4 |
| 6,369,243 B1 | 4/2002 | MacMillan et al. | 549/459 |
| 6,515,137 B2 * | 2/2003 | MacMillan et al. | 548/240 |
| 6,534,434 B2 * | 3/2003 | MacMillan et al. | 502/167 |
| 6,784,323 B2 | 8/2004 | MacMillan et al. | 568/459 |
| 2003/0236438 A1 | 12/2003 | MacMillian | 568/312 |

FOREIGN PATENT DOCUMENTS

WO    WO 92/02505    2/1992

OTHER PUBLICATIONS

Ahrendt et al., "New strategies for organic catalysis: the first highly enantioselective organocatalytic Diels-Alder reaction," J. Am. Chem. Soc. (2000) 122:4243-4244.
Burk et al., "Preparation and use of C2-symmetric bis(phospholanes): production of α-amino acid derivatives via highly enantioselective hydrogenation reactions," J. Am. Chem. Soc. (1993) 115:10125-10138.
Burk et al., "Enantioselective hydrogenation of the C=N group: a catalytic asymmetric reductive amination procedure," J. Am. Chem. Soc. (1992) 114:6266-6267.
Burk et al., "Asymmetric catalytic synthesis of β-branched amino acids via highly enantioselective hydrogenation reactions," J. Am. Chem. Soc. (1995) 117:9375-9376.
Burk et al., "New electron-rich chiral phosphines for asymmetric catalysis," Organometallics (1990) 9:2653-2655.
Cai et al., "Simple and efficient resolution of 1,1'-bi-2-naphthol," Tetrahedron Lett. (1995) 36:7991-7994.

Corey et al., "Highly enantioselective catalytic Diels-Alder addition promoted by a chiral bis(oxazoline)-magnesium complex," Tetrahedron Lett. (1992) 33:6807-6810.
Evans et al., "C2-symmetric copper(II) complexes as chiral Lewis acids. Catalytic enantioselective aldol additions of enolsilanes to pyruvate esters," J. Am. Chem. Soc. (1997) 119:7893-7894.
Evans et al., "Bis(oxazaline) copper(II) complexes as chiral catalysts for the enantioselective Diels-Alder reaction," J. Am. Chem. Soc (1993) 115:6460-6461.
Evans et al., "Bis(imine)-copper(II) complexes as chiral Lewis acid catalysts for the Diels-Alder reaction," Tetrahedron Lett. (1993) 34:7027-7030.
Evans et al., "Cationic bis(oxazolin) and pyridyl-bis(oxazoline) Cu(II) and Zn(II) Lewis acid catalysts. A comparative study in catalysis of Diels-Alder and Aldol reactions," Tetrahedron Lett. (1996) 37:7481-7484.
Gothelf et al., "Control of diastereo- and entioselectivity in metal-catalyzed 1,3-dipolar cycloaddition reactions of nitrones with alkenes. Experimental and theoretical investigations," J. Org. Chem. (1996) 61:346-355.
Jen et al., "New strategies for organic catalysis: the first enantioselective organocatalytic 1,3-dipolar cycloaddition," J. Am. Chem. Soc. (2000) 122:9874-9875.
Keck et al., "Catalytic asymmetric allylation of aldehydes," J. Am. Chem. Soc. (1993) 115:8467-8468.
Keck et al., "Pronounced solvent and concentration effects in an entioselective Mukaiyama Aldol condensation using BINOL-titanium(IV) catalysts," J. Am. Chem. Soc. (1995) 117:2363-2364.
Keinan and Greenspoon, "Partial Reduction of Enones, Styrenes and Related Systems," in Comprehensive Organic Synthesis, vol. 8, Trost and Fleming, eds., Chap 3.5, Pergamon Press, Oxford, pp. 524-578, 1991.
Kobasyashi et al., "Lanthanide(III)-catalyzed enantioselective Diels-Alder reactions. Stereoselective synthesis of both enantiomers by using a single chiral source and a choice of achiral ligands," J. Am. Chem. Soc. (1994) 116:4083-4084.
Lavilla, "Recent developments in the chemistry of dihydrophyridines," J. Chem. Soc. Perkin Trans. (2002) 1:1141-1156.
Li et al., "Asymmetric alkene aziridination with readily available chiral diimine-based catalysts," J. Am. Chem. Soc. (1993) 115:5326-5327.
Mikami et al., "Asymmetric glyoxylate-ene reaction catalyzed by chiral titanium complexes: a practical access to α-hydroxy esters in high enantiomeric purities," J. Am. Chem. Soc. (1989) 111:1940-1941.

(Continued)

*Primary Examiner*—Sikarl A. Witherspoon
(74) *Attorney, Agent, or Firm*—Isaac M. Rutenberg; Mintz, Levin, Cohn, Ferris, Glovsky, and Popeo, PC

(57) ABSTRACT

Nonmetallic, chiral organic catalysts are used to catalyze the 1,4-hydride reduction of an α,β-unsaturated carbonyl compound. The α,β-unsaturated carbonyl compound may be an aldehyde or cyclic ketone, and the hydride donor may be a dihydropyridine. The reaction is enantioselective, and proceeds with a variety of hydride donors, catalysts, and substrates. The invention also provides compositions effective in carrying out the 1,4-hydride addition of α,β-unsaturated carbonyl compounds.

13 Claims, No Drawings

OTHER PUBLICATIONS

Mikami et al., "Asymmetric catalysis of Diels-Alder cycloadditions by MS-free binaphthol-titanium complex: dramatic effect of MS, linear vs. positive nonlinear relationship, and synthetic applications," J. Am. Chem. Soc. (1994) 116:2812-2820.

Mikami et al., "Asymmetric catalytic aldol-type reaction with ketene silyl acetals: possible intervention of the silatropic ene pathway," J. Am. Chem. Soc. (1994) 116:4077-4078.

Miyashita et al., "Synthesis of 2,2'-bis(diphenylphosphino)-1,1'-binaphthyl (BINAP), an atropisomeric chiral bis(triaryl)phosphine, and its use in the rhodium(I)-catalyzed asymmetric hydrogenation of α-(acrylamino) acrylic acids," J. Am. Chem. Soc. (1980) 102:7932-7934.

Miyashita et al., "2,2'-Bis(diphenylphosphino)-1,1'-binaphthyl (BINAP)," Tetrahedron (1984) 40:1245-1253.

Noyori, "Asymmetric catalysis: science and opportunities (Nobel lecture)," Angew. Chem. Intl. Ed. (2002) 41:2008-2022.

Ouellet et al., "Enantioselective organocatalytic hydride reduction," J. Am. Chem. Soc. (2005) 127:32-33 (with supporting information).

Paras et al., "New strategies for organic catalysis: the first enantioselective organocatalytic Friedel-Crafts alkylation," J. Am. Chem. Soc. (2001) 123:4370-4371.

Stout and Meyers, "Recent advances in the chemistry of dihydropyridines," Chem. Rev. (1982) 82:223-243.

Takaya et al., "Practical synthesis of (R)- or (S)-2,2'-bis(diarylphosphino)-1,1'-binaphthyls (BINAPs)," J. Org. Chem. (1986) 51:629-635.

Takaya et al., "(R)-(+) and (S)-(−)-2,2'-Bis(diphenylphosphino)-1,1'-binaphthyl (BINAP)," (1988) Org. Synth 67:20-32.

Yang et al., "Design and synthesis of chiral ketones for catalytic asymmetric epoxidation of unfunctionalized olefins," J. Am. Chem. Soc. (1998) 120:5943-5952.

* cited by examiner

HYDRIDE REDUCTION OF α,β-UNSATURATED CARBONYL COMPOUNDS USING CHIRAL ORGANIC CATALYSTS

CROSS-REFERENCE TO RELATED APPLICATIONS

This application claims priority under 35 U.S.C. § 119(e)(1) to provisional U.S. Ser. Nos. 60/629,674, filed Nov. 19, 2004, and Ser. No. 60/642,700, filed Jan. 10, 2005, the disclosures of which are incorporated herein by reference in their entireties.

GOVERNMENT RIGHTS

The U.S. Government has certain rights in this invention pursuant to Grant No. R01 GM66142-01 awarded by the National Institutes of Health.

TECHNICAL FIELD

This invention relates generally to catalysis of enantioselective reactions, and more particularly relates to enantioselective reactions involving the use of chiral organic compounds as catalysts in the hydride reduction of α,β-unsaturated carbonyl compounds.

BACKGROUND OF THE INVENTION

Ancillary (or "spectator") ligand-metal coordination complexes (e.g., organometallic complexes) and compositions are useful as catalysts, stoichiometric reagents and therapeutic agents. The ancillary ligand contains functional groups that bind to one or more metal centers and remain associated therewith, providing an opportunity to modify the steric, electronic and chemical properties of the active sites of the complex, i.e., the metal centers.

Unfortunately, many organometallic reagents are expensive and depending on their catalytic activity may not be commercially viable. Moreover, many organometallic complexes are useful only for very specific chemical reactions and do not have broad utility as catalysts for a variety of different types of reactions. This problem may be emphasized for the catalysis of reactions leading to chiral molecules, particularly the conversion of either chiral or achiral molecules via enantioselective catalysis to provide a chiral product.

Over the last 30 years enantioselective catalysis has become one of the most important frontiers in exploratory organic synthetic research. In the pharmaceutical industry and other industries, the use of pure enantiomeric molecules is often important for safety and efficacy. Thus, in the production of pharmaceuticals, use of catalysts or reagents that preferentially produce one enantiomer of a molecule relative to another enantiomer is particularly advantageous. Unfortunately, the catalysts that produce such enantiomers are typically-organometallic complexes that are specific for a particular reaction. In addition, there is no way to predict with any reasonable accuracy which enantiomer will result. Examples of organometallic catalysts used to prepare chiral materials include BINOL-based complexes (Mikanii et al. (1994) *J. Am. Chem. Soc.* 116:2812; Kobayashi et al. (1994) *J. Am. Chem. Soc.* 116:4083; Mikami et al. (1989) *J. Am. Chem. Soc.* 111:1940; Mikami et al. (1994) *J. Am. Chem. Soc.* 116:4077; Keck et al. (1993) *J. Am. Chem. Soc.* 115:8467; Keck et al. (1995) *J. Am. Chem. Soc.* 117:2363), BINAP-based complexes (Miyashita et al. (1980) *J. Am. Chem. Soc.* 102:7932; Miyashita et al. (1984) *Tetrahedron* 40:1245; Takaya et al. (1986) *J. Org. Chem.* 51:629; Takaya et al. (1988) *Org. Synth.* 67:20; Cai et al. (1995) *Tetrahedron Lett.* 36:7991), DUPHOS complexes (Burk et al. (1990) *Organometallics* 9:2653; Burk et al. (1993) *J. Am. Chem. Soc.* 115:10125; Burk et al. (1992) *J. Am. Chem. Soc.* 114:6266; Burk et al. (1995) *J. Am. Chem. Soc.* 117:9375); salen-based complexes (i.e., organometallic complexes containing the N,N-bis(3,5-di-t-butylsalicylidene)-1,2-cyclohexane-diamino ligand; see, e.g., Li et al. (1993)*J. Am. Chem. Soc.* 115:5326, and Evans et al. (1993) *Tetrahedron Lett.* 34:7027), and bisoxazoline-containing compounds (Evans et al. (1993) *J. Am. Chem. Soc.* 115:6460; Evans et al. (1997) *J. Am. Chem. Soc.* 119:7893; Evans et al. (1996) *Tetrahedron Lett.* 37:7481; Corey et al. (1992) *Tetrahedron Lett.* 33:6807; Gothelf et al. (1996) *J. Org. Chem.* 61:346).

One aspect of catalysis that is of particular interest is 1,4-hydride addition (i.e., reduction) reactions involving α,β-unsaturated carbonyl compounds. Numerous reviews of hydride reduction reactions have been published, including Keinan et al., *Comprehensive Organic Synthesis*, Trost, Fleming, Eds; (Pergamon Press: Oxford, 1991) 8:523-578. Improved methods for chemoselectively and enantioselectively hydrogenating α,β-unsaturated carbonyls are desired by numerous disciplines in the chemical arts, including medicinal chemistry and materials science.

Despite the observed need and relatively few, narrow solutions, relatively few asymmetric transformations have been reported which employ organic molecules as reaction catalysts. There is tremendous potential for academic, economic and environmental benefit should versatile, chiral organic catalysts be developed. Only a few researchers have disclosed organic catalysts useful for preparing chiral materials. See, e.g., *Asymmetric Catalysis in Organic Synthesis*, Noyori, R., Ed. (New York: Wiley, 1994) and *Asymmetric Synthesis*, Ojima, I., Ed. (New York: VCH, 1993), and references cited therein. Also see Yang et al. (1998) *J. Am. Chem. Soc.* 120(24):5943-5952, who disclose the use of a dioxirane to catalyze enantioselective epoxidation, and Shi et al. (1995) *J. Chem. Research* (S):46-47 (*J. Chem. Research* (M): 0401-0411), who disclose preparation of chiral quaternary ammonium salts stated to be useful as chiral phase-transfer catalysts by reaction of (R)-(+)-2,2-bis(bromomethyl)-6,6-dinitrobiphenyl and (R)-(+)-2,2-bis(bromomethyl)-1,1-binaphthyl with cyclic amines such as pyrrolidine, piperidine and 4-hydroxypiperidine. International Patent Publication No. WO 92/02505 to Castelijns also discloses use of a secondary amine in a catalytic transformation, i.e., in conversion of an unsaturated imine to a pyridine product, by reaction with an aldehyde or ketone.

Recently, certain organic catalysts have been disclosed as useful in a variety of transformations, by lowering the LUMO (lowest unoccupied molecular orbital) of a reactant to facilitate reaction thereof. The organic catalysts are acid addition salts of nonmetallic compounds containing a Group 15 or Group 16 heteroatom, e.g., chiral amines, exemplified by the imidazolidinone salt (5S)-5-benzyl-2,2,3-trimethylimidazolidin-4-one hydrochloride (I)

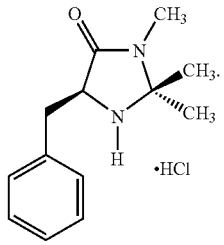
(I)

Such catalysts are described in U.S. Pat. No. 6,307,057 to MacMillan and U.S. Pat. No. 6,369,243 to MacMillan et al.

The use of catalyst (I) in the LUMO-lowering activation of α,β-unsaturated aldehydes, in particular, has been reported by Ahrendt et al. (2000) *J. Am. Chem. Soc.* 122: 4243-4244, Jen et al. (2000) *J. Am. Chem. Soc.* 122:9874-9875, and Paras et al. (2001) *J. Am. Chem. Soc.* 123:4370-4371. The reaction proceeds via the reversible formation of an iminium ion intermediate, which can be in one of two enantiomeric configurations.

While imidazolidinone salt (I) and other chiral amines described in the foregoing references are used as organic catalysts in, there is a continuing need for catalytic methods that provide high levels of enantioselectivity across a diverse range of α,β-unsaturated carbonyl compounds as reactants. An ideal catalytic method, in addition to providing high levels of enantioselectivity, would be efficient, would employ nonmetallic catalysts that are inexpensive and straightforward to synthesize, and could be carried out under aerobic conditions.

SUMMARY OF THE INVENTION

In one embodiment, then, the invention provides a process for catalyzing an enantioselective 1,4-hydride reduction of an α,β-unsaturated aldehyde to produce an aldehyde having a chiral carbon at the β-position. The process comprises contacting the α,β-unsaturated aldehyde a hydride donor in the presence of a catalyst comprising an acid addition salt of an imidazolidinone. The catalyst is capable of lowering the energy level of the lowest unoccupied molecular orbital of the α,β-unsaturated aldehyde, and the hydride donor is capable of reacting with the aldehyde by virtue of the lowered LUMO of the compound in the presence of the catalyst. The imidazolidinone has the structure of formula (IIA) or (IIB)

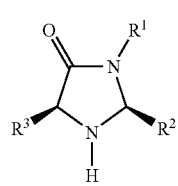
(IIA)

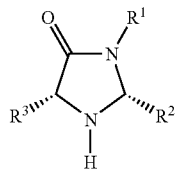
(IIB)

In formulae (IIA) and (IIB), $R^1$ is selected from $C_1$-$C_{24}$ hydrocarbyl, substituted $C_1$-$C_{24}$ hydrocarbyl, heteroatom-containing $C_1$-$C_{24}$ hydrocarbyl, and substituted heteroatom-containing $C_1$-$C_{24}$ hydrocarbyl. $R^2$ has the structure —$(L)_m$—$CR^4R^5R^6$ wherein m is zero or 1, L is $C_1$-$C_6$ alkylene, and $R^4$, $R^5$ and $R^6$ are $C_1$-$C_{24}$ hydrocarbyl. $R^3$ is selected from H, $C_1$-$C_{24}$ hydrocarbyl, substituted $C_1$-$C_{24}$ hydrocarbyl, heteroatom-containing $C_1$-$C_{24}$ hydrocarbyl, and substituted heteroatom-containing $C_1$-$C_{24}$ hydrocarbyl.

In another embodiment, the invention provides a process for catalyzing a 1,4-hydride reduction of an α,β-unsaturated cyclic ketone to produce a ketone product having a chiral carbon at the β-position. The process comprises contacting the α,β-unsaturated cyclic ketone with a dihydropyridine in the presence of a catalyst comprising an acid addition salt of an imidazolidinone. The catalyst is capable of lowering the energy level of the lowest unoccupied molecular orbital of the α,β-unsaturated cyclic ketone, and the dihydropyridine is capable of reacting with the ketone by virtue of the lowered LUMO of the compound in the presence of the catalyst.

In yet another embodiment, the invention provides a composition comprising a combination of a hydride donor and an imidazolidinone catalyst.

Further aspects, features, and advantages of the invention will be described elsewhere herein.

DETAILED DESCRIPTION OF THE INVENTION

Unless otherwise indicated, the invention is not limited to specific molecular structures, substituents, synthetic methods, reaction conditions, or the like, as such may vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a catalyst" includes a single catalyst as well as a combination or mixture of two or more catalysts, reference to "a reactant" encompasses a combination or mixture of different reactants as well as a single reactant, and the like.

In this specification and in the claims that follow, reference will be made to a number of terms, which shall be defined to have the following meanings:

The abbreviations Me, Et, n-Pr, i-Pr, n-butyl, i-butyl, t-Bu, Ph, and Bn represent methyl, ethyl, normal propyl, isopropyl, normal butyl, isobutyl, tert-butyl, phenyl, and benzyl, respectively.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and the terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein may, for example, may contain 1 to 3 carbon atoms, and as a further example, such substituents may contain 1 or 2 carbon atoms (i.e., methoxy and ethoxy).

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$), mono- and di-($C_1$-$C_{24}$ alkyl)-substituted phosphino, mono- and di-($C_5$-$C_{20}$ aryl)-substituted phosphino; and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and substituted aryl."

The terms "LUMO" and "HOMO" (abbreviations for lowest unoccupied molecular orbital and highest occupied molecular orbital, respectively) refer to the frontier orbitals of two reactants (such as an α,β-unsaturated carbonyl compound and a nucleophile), with the LUMO referring to the vacant orbital of lowest energy, in a first reactant (i.e., in an α,β-unsaturated aldehyde as described herein), and the HOMO referring to the orbital containing electrons of highest energy, in a second reactant.

The term "chiral" refers to a structure that does not have an improper rotation axis ($S_n$), i.e., it belongs to point group $C_n$ or $D_n$. Such molecules are thus chiral with respect to an axis, plane or center of asymmetry. "Chiral" molecules discussed herein are in enantiomerically pure form, such that a particular chiral molecule represents, for example, at least about 95 wt. % of the composition in which it is contained, as a further example at least about 99 wt. % of that composition.

The term "enantioselective" refers to a chemical reaction that preferentially results in one enantiomer relative to a second enantiomer, i.e., gives rise to a product of which a desired enantiomer represents at least about 50 wt. %.

Specification herein of the Group number of an atom is intended to identify the Group of the atom in the Periodic Table of the Elements following the current IUPAC convention.

Unless otherwise specified, reference to an atom is meant to include isotopes of that atom. For example, refence to H is meant to include $^1$H, $^2$H (i.e., D) and $^3$H (i.e., T), and reference to C is meant to include $^{12}$C and all isotopes of carbon (such as $^{13}$C).

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

Accordingly, the invention provides a method for using organic catalysts to carry out an enantioselective 1,4-hydride reduction reaction, to provide a carbonyl-containing compound, i.e., an aldehyde or ketone, having a chiral carbon in the β-position as an intermediate or final product.

In one embodiment of the invention, the reactant that is reduced in the 1,4-hydride addition reaction, i.e., the substrate, is an α,β-unsaturated cyclic ketone. In this embodiment, the catalyst is a nonmetallic chiral compound containing a Group 15 or Group 16 heteroatom, e.g., nitrogen, oxygen, sulfur or phosphorus, or a salt of such a compound. Oxygen-containing and sulfur-containing catalysts may be, for example, alcohols and thiols, respectively, while phosphorus-containing catalysts will generally be phosphines. Catalysts in which the heteroatom is a nitrogen atom may be primary amines, secondary amines or nitrogen-containing polymers. Amines may be secondary amines such as those having the structure of formula (III)

(III)

In formula (IV), $R^{10}$ and $R^{11}$ are selected from hydrogen, hydrocarbyl (e.g., alkyl, alkenyl, alkynyl, aryl, alkaryl, aralkyl, etc.), substituted hydrocarbyl (e.g., substituted alkyl, alkenyl, alkynyl, aryl, alkaryl, aralkyl, etc.), heteroatom-containing hydrocarbyl (e.g., heteroatom-containing alkyl, alkenyl, alkynyl, aryl, alkaryl, aralkyl, etc.), and substituted heteroatom-containing hydrocarbyl (e.g., substituted heteroatom-containing alkyl, alkenyl, alkynyl, aryl, alkaryl, aralkyl, etc.), or $R^{10}$ and $R^{11}$ are taken together to form a substituted or unsubstituted ring structure optionally containing a further heteroatom in addition to the nitrogen atom shown in formula (IV). When $R^{10}$ and $R^{11}$ are linked, the ring formed may be, for example, a five- or six-membered alicyclic or aromatic group, e.g., $R^{10}$ and $R^{11}$ may together form substituted or unsubstituted cyclopentyl, cyclohexyl, pyrrolidinyl, piperidinyl, morpholinyl, pyrrolyl, pyridinyl, pyrimidinyl, imidazolyl, or the like. Example compounds are those wherein $R^{10}$ and $R^{11}$ are independently selected from methyl, ethyl, propyl, butyl, cyclopentyl, cyclohexyl, cyclooctyl, phenyl, naphthyl, benzyl and trimethylsilyl, or are linked to form a 3- to 15-membered, optionally substituted cyclic moiety having the structure of formula (IV)

(IV)

wherein n is 0 or 1, X is a moiety that contains up to 50 atoms and is selected from hydrocarbylene, substituted hydrocarbylene, heteroatom-containing hydrocarbylene and substituted heteroatom-containing hydrocarbylene, and $X^1$ and $X^2$ are independently substituted or unsubstituted methylene. Examples of such secondary amines have the structure of formula (V)

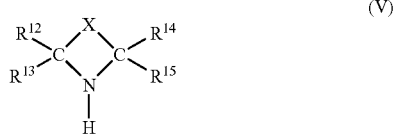

(V)

in which $R^{12}$, $R^{13}$, $R^{14}$, and $R^{15}$ are independently selected from hydrogen, $C_1$-$C_{24}$ hydrocarbyl (e.g., alkyl, alkenyl, alkynyl, aryl, alkaryl, aralkyl, etc.), substituted $C_1$-$C_{24}$ hydrocarbyl (e.g., substituted alkyl, alkenyl, alkynyl, aryl, alkaryl, aralkyl, etc.), heteroatom-containing $C_1$-$C_{24}$ hydrocarbyl (e.g., heteroatom-containing alkyl, alkenyl, alkynyl, aryl, alkaryl, aralkyl, etc.), substituted heteroatom-containing $C_1$-$C_{24}$ hydrocarbyl (e.g., substituted heteroatom-containing alkyl, alkenyl, alkynyl, aryl, alkaryl, aralkyl, etc.), and functional groups. As a further example, $R^{12}$, $R^{13}$, $R^{14}$, and $R^{15}$ are independently selected from hydrogen, hydroxyl, sulfhydryl, carboxyl, amino, mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_1$-$C_{24}$ aryl)-substituted amino, di-N-($C_1$-$C_{24}$ alkyl)-N-($C_5$-$C_{24}$ aryl)-substituted amino, $C_2$-$C_{24}$ alkylamido, $C_6$-$C_{24}$ arylamido, imino, $C_2$-$C_{24}$ alkylimino, $C_6$-$C_{24}$ arylimino, nitro, nitroso, $C_1$-$C_{24}$ alkoxy, $C_1$-$C_{24}$ aryloxy, $C_6$-$C_{24}$ aralkyloxy, $C_2$-$C_{24}$ alkylcarbonyl, $C_6$-$C_{24}$ arylcarbonyl, $C_2$-$C_{24}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, carbamoyl, mono-($C_1$-$C_{24}$ alkyl)-substituted carbamoyl, di-($C_1$-$C_{24}$ alkyl)-substituted carbamoyl, di-N-($C_1$-$C_{24}$ alkyl)-N-($C_5$-$C_{24}$ aryl)-substituted carbamoyl, mono-($C_5$-$C_{24}$ aryl)-substituted carbamoyl, di-($C_5$-$C_{24}$ aryl)-substituted carbamoyl, thiocarbamoyl, mono-($C_1$-$C_{24}$ alkyl)-substituted thiocarbamoyl, di-($C_1$-$C_{24}$ alkyl)-substituted thiocarbamoyl, di-N-($C_1$-$C_{24}$ alkyl)-N-($C_5$-$C_{24}$ aryl)-substituted thiocarbamoyl, mono-($C_5$-$C_{24}$ aryl)-substituted thiocarbamoyl, di-($C_5$-$C_{24}$ aryl)-substituted thiocarbamoyl, carbamido, formyl, thioformyl, sulfo, sulfonato, $C_1$-$C_{24}$ alkylthio, $C_5$-$C_{24}$ arylthio, $C_1$-$C_{24}$ alkyl, substituted $C_1$-$C_{24}$ alkyl, $C_1$-$C_{24}$ heteroalkyl, substituted $C_1$-$C_{24}$ heteroalkyl, $C_5$-$C_{24}$ aryl, substituted $C_5$-$C_{24}$ aryl, $C_1$-$C_{24}$ heteroaryl, substituted $C_1$-$C_{24}$ heteroaryl, $C_2$-$C_{24}$ aralkyl, substituted $C_6$-$C_{24}$ aralkyl, $C_2$-$C_{24}$ heteroaralkyl, and substituted $C_2$-$C_{24}$ heteroaralkyl, or $R^{12}$ and $R^{13}$, and/or $R^{14}$ and $R^{15}$, may together form an oxo moiety $=O$.

X may be, for example, $-(CR^{16}R^{17})-(X^3)_q-(CR^{18}R^{19})_t-$, in which case the amine has the structure of formula (VI)

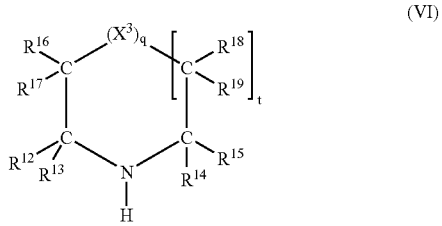

(VI)

wherein $X^3$ is O, S, NH, $NR^{20}$, or $CR^{21}R^{22}$, q is zero or 1, t is zero or 1, and $R^{16}$, $R^{17}$, $R^{18}$, $R^{19}$, $R^{21}$, and $R^{22}$ are independently selected from hydrogen, $C_1$-$C_{24}$ hydrocarbyl (e.g., alkyl, alkenyl, alkynyl, aryl, alkaryl, aralkyl, etc.), substituted $C_1$-$C_{24}$ hydrocarbyl (e.g., substituted alkyl, alkenyl, alkynyl, aryl, alkaryl, aralkyl, etc.), heteroatom-containing $C_1$-$C_{24}$ hydrocarbyl (e.g., heteroatom-containing alkyl, alkenyl, alkynyl, aryl, alkaryl, aralkyl, etc.), substituted heteroatom-containing $C_1$-$C_{24}$ hydrocarbyl (e.g., substituted heteroatom-containing alkyl, alkenyl, alkynyl, aryl, alkaryl, aralkyl, etc.), and functional groups. As a further example, $R^{16}$, $R^{17}$, $R^{18}$, $R^{19}$, $R^{21}$, and $R^{22}$ are independently selected from hydrogen, hydroxyl, sulfhydryl, carboxyl, amino, mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, di-N-($C_1$-$C_{24}$ alkyl)-N-($C_5$-$C_{24}$ aryl)-substituted amino, $C_2$-$C_{24}$ alkylamido, $C_6$-$C_{24}$ arylamido, imino, $C_2$-$C_{24}$ alkylimino, $C_6$-$C_{24}$ arylimino, nitro, nitroso, $C_1$-$C_{24}$ alkoxy, $C_5$-$C_{24}$ aryloxy, $C_6$-$C_{24}$ aralkyloxy, $C_2$-$C_{24}$ alkylcarbonyl, $C_6$-$C_{24}$ arylcarbonyl, $C_2$-$C_{24}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, carbamoyl, mono-($C_1$-$C_{24}$ alkyl)-substituted carbamoyl, di-($C_1$-$C_{24}$ alkyl)-substituted carbamoyl, di-N-($C_1$-$C_{24}$ alkyl)-N-($C_5$-$C_{24}$ aryl)-substituted carbamoyl, mono-($C_5$-

$C_{24}$ aryl)-substituted carbamoyl, di-($C_5$-$C_{24}$ aryl)-substituted carbamoyl, thiocarbamoyl, mono-($C_1$-$C_{24}$ alkyl)-substituted thiocarbamoyl, di-($C_1$-$C_{24}$ alkyl)-substituted thiocarbamoyl, di-N-($C_1$-$C_{24}$ alkyl)-N-($C_5$-$C_{24}$ aryl)-substituted thiocarbamoyl, mono-($C_5$-$C_{24}$ aryl)-substituted thiocarbamoyl, di-($C_5$-$C_{24}$ aryl)-substituted thiocarbamoyl, carbamido, formyl, thioformyl, sulfo, sulfonato, $C_1$-$C_{24}$ alkylthio, $C_5$-$C_{24}$ arylthio, $C_1$-$C_{24}$ alkyl, substituted $C_1$-$C_{24}$ alkyl, $C_1$-$C_{24}$ heteroalkyl, substituted $C_1C_{24}$ heteroalkyl, $C_5$-$C_{24}$ aryl, substituted $C_5$-$C_{24}$ aryl, $C_1$-$C_{24}$ heteroaryl, substituted $C_1$-$C_{24}$ heteroaryl, $C_2$-$C_{24}$ aralkyl, substituted $C_6$-$C_{24}$ aralkyl, $C_2$-$C_{24}$ heteroaralkyl, and substituted $C_2$-$C_{24}$ heteroaralkyl, or $R^{16}$ and $R^{17}$, and/or $R^{18}$ and $R^{19}$, together form an oxo moiety =O; and $R^{20}$ is selected from $C_1$-$C_{12}$ hydrocarbyl, substituted $C_1$-$C_{12}$ hydrocarbyl, heteroatom-containing $C_1$-$C_{12}$ hydrocarbyl, and substituted heteroatom-containing $C_1$-$C_{12}$ hydrocarbyl.

As an example, in formula (VI), q is zero, t is 1, and at least one of $R^{12}$ through $R^{15}$ is an acidic substituent such as a carboxyl group, such that the compound is proline or substituted proline. An example catalyst is L-proline per se, which, as will be appreciated by those of ordinary skill in the art, corresponds to the structure of formula (VI) when $R^{12}$ through $R^{14}$ and $R^{16}$ through $R^{19}$ are hydrogen, and $R^{15}$ is β-carboxyl.

In another embodiment of the invention, the substrate that undergoes 1,4-hydride addition is an α,β-unsaturated aldehyde. In this embodiment, the catalyst employed has the structure of formula (VI) wherein q is 1, $X^3$ is $NR^{20}$, t is zero, $R^{12}$ and $R^{14}$ are hydrogen, such that the secondary amine is a chiral imidazolidinone having the structure of formula (VIIA) or (VIIB)

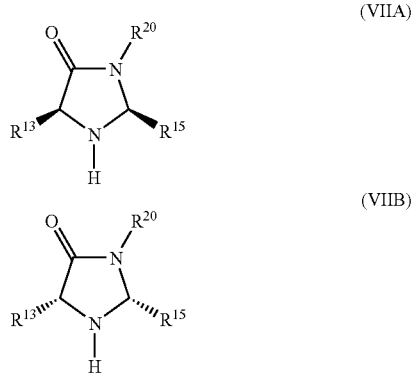

wherein the various substituents are as follows:

$R^{15}$ is as defined previously, and may be, for example, monocyclic aryl or heteroaryl optionally substituted with 1, 2, 3 or 4 substituents selected from halo, hydroxyl, and $C_1$-$C_{12}$ hydrocarbyl. As another example, $R^{15}$ may be methylfuranyl (e.g., 5-methyl-furan-2-yl) or phenyl. In a further example, $R^{15}$ may have the structure -(L)$_m$—$CR^{23}R^{24}R^{25}$ wherein m is zero or 1, L is $C_1$-$C_6$ alkylene, and $R^{23}$, $R^{24}$ and $R^{25}$ are $C_1$-$C_{12}$ hydrocarbyl. In yet another example, $R^{15}$ substituents are those wherein m is zero and $R^{23}$, $R^{24}$ and $R^{25}$ are $C_1$-$C_{12}$ alkyl. In a further example, $R^{23}$, $R^{24}$ and $R^{25}$ are $C_1$-$C_6$ alkyl, e.g., methyl (such that $R^{15}$ is then a tert-butyl group).

$R^{20}$ is selected from $C_1$-$C_{24}$ hydrocarbyl (e.g., alkyl, alkenyl, alkynyl, aryl, alkaryl, aralkyl, etc.), substituted $C_1$-$C_{24}$ hydrocarbyl (e.g., substituted alkyl, alkenyl, alkynyl, aryl, alkaryl, aralkyl, etc.), heteroatom-containing $C_1$-$C_{24}$ hydrocarbyl (e.g., heteroatom-containing alkyl, alkenyl, alkynyl, aryl, alkaryl, aralkyl, etc.), and substituted heteroatom-containing $C_1$-$C_{24}$ hydrocarbyl (e.g., substituted heteroatom-containing alkyl, alkenyl, alkynyl, aryl, alkaryl, aralkyl, etc.). Examples of $R^{20}$ substituents are $C_1$-$C_{12}$ hydrocarbyl such as $C_1$-$C_{12}$ alkyl, with $C_1$-$C_6$ alkyl groups (e.g., Me, Et, i-Pr, t-Bu) as a further example.

$R^{13}$ is as defined previously, and may be, for example, hydrogen, $C_1$-$C_{24}$ alkyl, substituted $C_1$-$C_{24}$ alkyl, $C_1$-$C_{24}$ heteroalkyl, substituted $C_1$-$C_{24}$ heteroalkyl, $C_5$-$C_{24}$ aryl, substituted $C_5$-$C_{24}$ aryl, $C_1$-$C_{24}$ heteroaryl, substituted $C_1$-$C_{24}$ heteroaryl, $C_6$-$C_{24}$ aralkyl, substituted $C_6$-$C_{24}$ aralkyl, $C_2$-$C_{24}$ heteroaralkyl, and substituted $C_2$-$C_{24}$ heteroaralkyl. As a further example, $R^{13}$ may be $C_6$-$C_{24}$ aralkyl, substituted $C_6$-$C_{24}$ aralkyl, $C_2$-$C_{24}$ heteroaralkyl, and substituted $C_2$-$C_{24}$ heteroaralkyl. In one embodiment, $R^{13}$ is —$CR^{26}R^{27}R^{28}$.

$R^{26}$ and $R^{27}$ are independently selected from hydrogen, halo, hydroxyl, $C_1$-$C_{12}$ hydrocarbyl, substituted $C_1$-$C_{12}$ hydrocarbyl, heteroatom-containing $C_1$-$C_{12}$ hydrocarbyl, and substituted heteroatom-containing $C_1$-$C_{12}$ hydrocarbyl. In one embodiment, $R^{26}$ and $R^{27}$ are hydrogen or $C_1$-$C_{12}$ hydrocarbyl, and, in a further embodiment, $R^{26}$ and $R^{27}$ are both hydrogen.

$R^{28}$ is a cyclic group optionally substituted with 1, 2, 3 or 4 non-hydrogen substituents and containing zero, 1, 2 or 3 heteroatoms generally selected from N, O, and S. As an example, $R^{28}$ is monocyclic aryl or heteroaryl optionally substituted with 1, 2, 3 or 4 substituents selected from halo, hydroxyl, and $C_1$-$C_{12}$ hydrocarbyl. As a further example, $R^{28}$ is phenyl optionally substituted with 1 or 2 substituents selected from halo, hydroxyl, and $C_1$-$C_6$ alkyl, and as an example embodiment, $R^{28}$ is an unsubstituted phenyl group.

As another embodiment, the catalysts may be chiral imidazolidinone compounds having the structure of formula (VIIA) or (VIIB) wherein the various substituents are as follows:

$R^{20}$ is selected from $C_1$-$C_{12}$ hydrocarbyl, substituted $C_1$-$C_{12}$ hydrocarbyl, heteroatom-containing $C_1$-$C_{12}$ hydrocarbyl, and substituted heteroatom-containing $C_1$-$C_{12}$ hydrocarbyl;

$R^{15}$ is selected from $C_1$-$C_{24}$ alkyl, $C_5$-$C_{24}$ alkaryl, $C_5$-$C_{24}$ aryl, and $C_5$-$C_{24}$ heteroaryl, any of which may be optionally substituted with 1, 2, 3 or 4 substituents selected from halo, hydroxyl, and $C_1$-$C_{12}$ hydrocarbyl;

$R^{13}$ can be, for example, hydrogen, monocyclic aryl, heteroaryl, or aralkyl optionally substituted with 1, 2, 3, or 4 substituents selected from halo, hydroxyl, and $C_1$-$C_{12}$ hydrocarbyl. As an example, then, $R^{15}$ is selected from substituted or unsubstituted $C_1$-$C_{12}$ alkyl, $C_5$-$C_{12}$ alkaryl, $C_5$-$C_5$-$C_{12}$ aryl, and $C_1$-$C_{12}$ heteroaryl, and $R^{13}$ is selected from hydrogen and substituted or unsubstituted $C_1$-$C_{12}$ alkyl, $C_5$-$C_{12}$ alkaryl or $C_1$-$C_{12}$ aryl. As a further example, $R^{15}$ is Me, Et, Pr, i-Pr, Bu, t-Bu, Ph, Bn (i.e., $CH_2C_6H_5$), or 5-methyl-furan-2-yl, and $R^{13}$ is H, Me, Et, Pr, i-Pr, Bu, t-Bu, Ph, or Bn.

As a still further example, the catalyst may be a chiral imidazolidinone having the structure of formula (IIA) or (IIB)

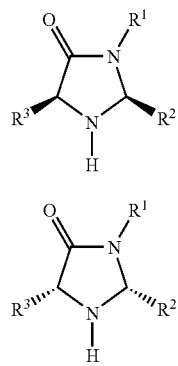

wherein, in formulae (IIA) and (IIB), the various substituents are as follows:

$R^1$ is selected from $C_1$-$C_{24}$ hydrocarbyl (e.g., alkyl, alkenyl, alkynyl, aryl, alkaryl, aralkyl, etc.), substituted $C_1$-$C_{24}$ hydrocarbyl (e.g., substituted alkyl, alkenyl, alkynyl, aryl, alkaryl, aralkyl, etc.), heteroatom-containing $C_1$-$C_{24}$ hydrocarbyl (e.g., heteroatom-containing alkyl, alkenyl, alkynyl, aryl, alkaryl, aralkyl, etc.), and substituted heteroatom-containing $C_1$-$C_{24}$ hydrocarbyl (e.g., substituted heteroatom-containing alkyl, alkenyl, alkynyl, aryl, alkaryl, aralkyl, etc.). Examples of $R^1$ substituents are $C_1$-$C_{12}$ hydrocarbyl such as $C_1$-$C_{12}$ alkyl, with $C_1$-$C_6$ alkyl groups (e.g., Me, Et, i-Pr, t-Bu) as a further example.

$R^2$ is selected from H, $C_1$-$C_{24}$ hydrocarbyl (e.g., alkyl, alkenyl, alkynyl, aryl, alkaryl, aralkyl, etc.), substituted $C_1$-$C_{24}$ hydrocarbyl (e.g., substituted alkyl, alkenyl, alkynyl, aryl, alkaryl, aralkyl, etc.), heteroatom-containing $C_1$-$C_{24}$ hydrocarbyl (e.g., heteroatom-containing alkyl, alkenyl, alkynyl, aryl, alkaryl, aralkyl, etc.), and substituted heteroatom-containing $C_1$-$C_{24}$ hydrocarbyl. As an example, $R^2$ has the structure -$(L)_m$—$CR^4R^5R^6$ wherein m is zero or 1, L is $C_1$-$C_6$ alkylene, and $R^4$, $R^5$ and $R^6$ are $C_1$-$C_{24}$ hydrocarbyl. As a further example, $R^2$ is t-Bu.

$R^3$ is selected from H, $C_1$-$C_{24}$ hydrocarbyl (e.g., alkyl, alkenyl, alkynyl, aryl, alkaryl, aralkyl, etc.), substituted $C_1$-$C_{24}$ hydrocarbyl (e.g., substituted alkyl, alkenyl, alkynyl, aryl, alkaryl, aralkyl, etc.), heteroatom-containing $C_1$-$C_{24}$ hydrocarbyl (e.g., heteroatom-containing alkyl, alkenyl, alkynyl, aryl, alkaryl, aralkyl, etc.), and substituted heteroatom-containing $C_1$-$C_{24}$ hydrocarbyl. As an example, $R^3$ is selected from H and —$CR^7R^8R^9$ wherein $R^7$ and $R^8$ are independently selected from hydrogen, halo, hydroxyl, $C_1$-$C_{24}$ hydrocarbyl, substituted $C_1$-$C_{24}$ hydrocarbyl, heteroatom-containing $C_1$-$C_{24}$ hydrocarbyl, substituted heteroatom-containing $C_1$-$C_{24}$ hydrocarbyl, and $R^9$ is a cyclic group optionally substituted with 1, 2, 3 or 4 non-hydrogen substituents and containing zero, 1, 2 or 3 heteroatoms. As a further example, $R^3$ is selected from H, Bn, and Ph.

The catalysts are chiral with respect to an axis, plane or center of asymmetry, but are generally chiral with a center of asymmetry present. It will be appreciated by those skilled in the art that the various R groups discussed with respect to the foregoing amines can be selected to create the desired chirality.

Any of the aforementioned catalysts may also be employed in the present reactions in the form of an acid addition salt. That is, the catalyst may be incorporated into the reaction mixture as an acid addition salt, or an acid may be added to the reaction mixture to serve as a co-catalyst. The acid used to form the salt or employed as a co-catalyst for the electronically neutral compound is generally, although not necessarily, a Brønsted acid. Suitable Brønsted acids generally, although not necessarily, have a pKa of less than about 5. Combinations of Brønsted acids may also be used. Suitable acids include both organic and inorganic acids, with inorganic acids including, but not limited to, hydrochloric acid, hydrobromic acid, sulfuric acid, sulfurous acid, nitric acid, nitrous acid, perchloric acid, phosphoric acid, and chromic acid, and with organic acids being, for example, carboxylic acids, sulfonic acids, phosphonic acids, and aromatic alcohols, e.g., phenols, substituted with 1 to 5 electron-withdrawing substituents such as nitro, cyano, sulfonato, halo (i.e., Cl, F, Br or I) and halogenated alkyl (typically fluorinated alkyl, preferably perfluorinated lower alkyl such as trifluoromethyl). Examples of suitable organic acids are carboxylic acids and sulfonic acids having the structural formulas $R^x$—COOH and $R^x$—$SO_2$—OH wherein $R^x$ is aryl, alkyl, substituted aryl (e.g., halogenated aryl), or substituted alkyl (e.g., halogenated alkyl, particularly fluorinated and chlorinated alkyl). Examples of $R^x$ groups are methyl, halogenated methyl (e.g., fluorinated methyl such as trifluoromethyl, chlorinated methyl such as chloromethyl, dichloromethyl, and trichloromethyl, etc.), and nitrite-substituted methyl. Specific examples of preferred organic acids include acetic acid, propionic acid, glycolic acid, pyruvic acid, oxalic acid, malic acid, malonic acid, succinic acid, maleic acid, fumaric acid, tartaric acid, citric acid, benzoic acid, 2-nitrobenzoic acid, cinnamic acid, mandelic acid, methanesulfonic acid, ethanesulfonic acid, triflic acid, p-toluene sulfonic acid, p-toluene sulfinic acid, salicylic acid, chloroacetic acid, dichloroacetic acid, trichloroacetic acid, trifluoroacetic acid, and combinations thereof. The Brønsted acid may or may not be polymer-bound, and may or may not be in the form of a hydrate (e.g., mono-, di-, tri-, tetra- or pentahydrate). The Brønsted acid may or may not be chiral, and those Brønsted acids that are chiral may be used in isomerically pure form or as a racemic mixture.

Acid addition salts may be synthesized by admixing the electronically neutral form of the catalyst (e.g., an imidazolidinone of formula IIA, IIB, VIIA or VIIB) with a Brønsted acid $HX^A$, at a desired molar ratio, generally in the range of approximately 1:100 to 100:1, typically about 1:10 to 10:1, preferably about 1:2 to 2:1. Alternatively, the uncharged catalyst may be combined with at least one salt $[M^{z+}]$ $z[X^A]^-$, thereby forming the desired salt via ion exchange. A wide variety of salts may be used for this latter purpose, and the cation $M^{+z}$ can be virtually any cation, although z is generally 1, 2 or 3. Suitable M elements are typically chosen from Groups 2 to 13 of the Periodic Table of the Elements, but M may also be a polyatomic cation such as the ammonium ion $NH_4^+$. It should also be noted that the salt form of the catalyst can be prepared with two or more different Brønsted acids or metal salts, thereby forming a mixture of salts, i.e., salts containing different anions $[X^A]^-$.

For purposes of exemplification, a detailed description of one method for synthesizing the imidazolidinone salt (2S, 5S)-5-benzyl-2-tert-butyl-3-methylimidazolidin-4-one hydrochloride ((5S)-5-benzyl-2,2,3-trimethylimidazolidin-4-one hydrochloride) is described in Example 1.

Aldehyde Substrates:

The α,β-unsaturated aldehyde has the structure of formula (VIII)

(VIII)

in which $R^{29}$, $R^{30}$ and $R^{31}$ are independently selected from hydrogen, $C_1$-$C_{30}$ hydrocarbyl, heteroatom-containing $C_1$-$C_{30}$ hydrocarbyl, substituted $C_1$-$C_{30}$ hydrocarbyl, substituted heteroatom-containing $C_1$-$C_{30}$ hydrocarbyl, and functional groups, and any two of $R^{29}$, $R^{30}$ and $R^{31}$ taken together can form a cyclic structure. As an example, $R^{29}$, $R^{30}$ and $R^{31}$ are independently selected from hydrogen, $C_1$-$C_{24}$ alkyl, $C_2$-$C_{24}$ alkenyl, $C_2$-$C_{24}$ alkynyl, $C_1$-$C_{24}$ alkoxy, $C_2$-$C_{24}$ alkenyloxy, $C_2$-$C_{24}$ alkynyloxy, $C_5$-$C_{30}$ aryl, $C_5$-$C_{30}$ aryloxy, $C_5$-$C_{30}$ haloaryl, $C_5$-$C_{30}$ nitroaryl, $C_2$-$C_{24}$ alkoxyalkyl, $C_6$-$C_{30}$ aryloxyalkyl, hydroxyl, sulfhydryl, $C_2$-$C_{24}$ alkylcarbonyl, $C_6$-$C_{30}$ arylcarbonyl, $C_2$-$C_{24}$ alkoxycarbonyl, $C_6$-$C_{30}$ aryloxycarbonyl, halocarbonyl, $C_2$-$C_{24}$ alkylcarbonato, $C_6$-$C_{30}$ arylcarbonato, carboxy, carboxylato, carbamoyl, mono- and di-($C_1$-$C_{24}$ alkyl)-substituted carbamoyl, mono- and di-($C_5$-$C_{20}$ aryl)-substituted carbamoyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{30}$ arylamido, imino, $C_2$-$C_{24}$ alkylimino, $C_6$-$C_{30}$ arylimino, nitro, nitroso, sulfo, sulfonato, $C_1$-$C_{24}$ alkylsulfanyl, $C_5$-$C_{30}$ arylsulfanyl, $C_1$-$C_{24}$ alkylsulfinyl, $C_5$-$C_{30}$ arylsulfinyl, $C_1$-$C_{24}$ alkylsulfonyl, $C_5$-$C_{30}$ arylsulfonyl, phosphono, phosphonato, phosphinato, phospho, phosphino, and combinations thereof. In addition, any two of $R^{29}$, $R^{30}$ and $R^{3'}$ taken together can form a cyclic structure selected from five-membered rings, six-membered rings, and fused five-membered and/or six-membered rings, wherein the cyclic structure is aromatic, alicyclic, heteroaromatic, or heteroalicyclic, and has zero, 1, 2, 3 or 4 non-hydrogen substituents and zero, 1, 2 or 3 heteroatoms.

As a further example, $R^{29}$ is hydrogen, and $R^{30}$ and $R^{3'}$ are independently selected from hydrogen, $C_1$-$C_{12}$ alkyl, $C_1$-$C_{12}$ alkoxy, $C_5$-$C_{20}$ aryl, $C_2$-$C_{12}$ alkoxyalkyl, $C_2$-$C_{12}$ alkoxycarbonyl, $C_6$-$C_{20}$ aryloxycarbonyl, and $C_6$-$C_{20}$ aryloxyalkyl. As a still further example, $R^{30}$ and $R^{3'}$ are selected from hydrogen, $C_1$-$C_6$ alkyl, $C_5$-$C_{12}$ aryl, $C_2$-$C_6$ alkoxycarbonyl, $C_6$-$C_{12}$ aryloxycarbonyl, and $C_6$-$C_{12}$ aryloxyalkyl, e.g., methyl, ethyl, phenyl, benzyl, benzoyloxy, halophenyl, nitrophenyl, etc.

The α,β-unsaturated aldehydes having the structure of formula (VIII) may be in either the E- or the Z-configuration. The isomeric purity of the α,β-unsaturated aldehyde is not critical. That is, the α,β-unsaturated aldehyde may be essentially isomerically pure (i.e., consisting of essentially pure E- or essentially pure Z-isomer) or may be a mixture of E- and Z-isomers wherein the mixture may range from 50:50 E:Z to essentially pure E- or essentially pure Z-isomer. For example, when a mixture, the α,β-unsaturated aldehyde may comprise an E:Z ratio of 10:90, 20:80, 30:70, 40:60, 50:50, 60:40, 70:30, 80:20, or 90:10.

The product of the catalyzed 1,4-hydride reduction of an α,β-unsaturated aldehyde is an aldehyde having a chiral carbon moiety in the β-position relative to the carbonyl carbon (i.e., a β-chiral aldehyde). While the isomeric purity of the α,β-unsaturated aldehyde is not critical (as explained infra), the 1,4-hydride reductions of the invention may be characterized as enantioselective in that one enantiomer of the product is preferentially produced over any other possible enantiomers. Without wishing to be bound by theory, it is believed that the catalyst forms an iminium ion complex with the substrate (i.e., the α,β-unsaturated aldehyde), and that the iminium ion complex isomerizes the substrate to a preferred conformation before the complex reacts with the hydride donor. The preferred conformation of the iminium ion complex is dependent upon the stereochemistry of the catalyst. Thus, 1,4-hydride reductions that are carried out using substrates of opposite stereochemistry (i.e., E- or Z-isomers) may yield products with the same stereochemistry. That is, the 1,4-hydride reductions of the invention may be characterized as stereoconvergent, preferentially producing one enantiomer from a substrate comprising a mixture of isomers.

Because of the enantioselectivity of the reaction, a product from the 1,4-hydride reductions of the invention involving a α,β-unsaturated aldehyde may be a β-chiral aldehyde with an enantiomeric excess of, for example, above 50%. As a further example, the enantiomeric excess of the product may be above 75%, as a further example above 85%, and as a still further example above 90%.

Cyclic Ketone Substrates:

As explained above, the reactant undergoing 1,4-hydride addition is, in another embodiment, an α,β-unsaturated cyclic ketone. The ketone has the structure of formula (IX)

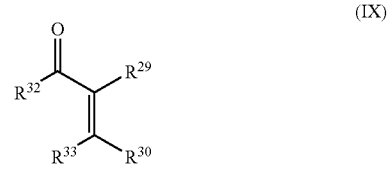

(IX)

in which $R^{29}$ and $R^{30}$ are as defined above, $R^{32}$ and $R^{33}$ are independently selected from $C_1$-$C_{30}$ hydrocarbyl, heteroatom-containing $C_1$-$C_{30}$ hydrocarbyl, substituted $C_1$-$C_{30}$ hydrocarbyl, substituted heteroatom-containing $C_1$-$C_{30}$ hydrocarbyl, and functional groups, and $R^{32}$ and $R^{33}$ are further linked to form a cycle. As an example, $R^{32}$ and $R^{33}$ are independently selected from $C_1$-$C_{24}$ alkyl, $C_2$-$C_{24}$ alkenyl, $C_2$-$C_{24}$ alkynyl, $C_1$-$C_{24}$ alkoxy, $C_2$-$C_{24}$ alkenyloxy, $C_2$-$C_{24}$ alkynyloxy, $C_5$-$C_{30}$ aryl, $C_5$-$C_{30}$ aryloxy, $C_5$-$C_{30}$ haloaryl, $C_5$-$C_{30}$ nitroaryl, $C_2$-$C_{24}$ alkoxyalkyl, $C_6$-$C_{30}$ aryloxyalkyl, hydroxyl, sulfhydryl, $C_2$-$C_{24}$ alkylcarbonyl, $C_6$-$C_{30}$ arylcarbonyl, $C_2$-$C_{24}$ alkoxycarbonyl, $C_6$-$C_{30}$ aryloxycarbonyl, halocarbonyl, $C_2$-$C_{24}$ alkylcarbonato, $C_6$-$C_{30}$ arylcarbonato, carboxy, carboxylato, carbamoyl, mono- and di-($C_1$-$C_{24}$ alkyl)-substituted carbamoyl, mono- and di-($C_5$-$C_{20}$ aryl)-substituted carbamoyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{30}$ arylamido, imino, $C_2$-$C_{24}$ alkylimino, $C_6$-$C_{30}$ arylimino, $C_1$-$C_{24}$ alkylsulfanyl, $C_5$-$C_{30}$ arylsulfanyl, $C_1$-$C_{24}$ alkylsulfinyl, $C_5$-$C_{30}$ arylsulfinyl, $C_1$-$C_{24}$ alkylsulfonyl, $C_5$-$C_{30}$ arylsulfonyl, mono- and di-($C_1$-$C_{24}$ alkyl)-substituted phosphino, mono- and di-($C_5$-$C_{20}$ aryl)-substituted phosphino, and combinations thereof. Furthermore, $R^{32}$ and $R^{33}$ may be linked to form a cycle comprising 5, 6, 7, 8, 9, 10, 11, 12 or more atoms. Still further, $R^{32}$ and $R^{33}$ may together form a cyclic structure comprising fused rings (containing 2, 3, 4, 5 or more rings, each of which being independently selected from 5-, 6-, 7-, 8- and higher-member rings), bridged rings (containing 2, 3, 4, 5, 6 or more bridge atoms), or combinations thereof, wherein the cyclic structure is aromatic, alicyclic, heteroaromatic, or heteroalicyclic, and has zero, 1, 2, 3, 4, 5, 6 or more non-hydrogen substituents and zero, 1, 2, 3 or more heteroatoms. In addition, any two of $R^{29}$, $R^{30}$ and $R^{32}$ may be linked to form a cycle, and any two of $R^{29}$, $R^{30}$, and $R^{33}$ may be linked to form a cycle. For example, $R^{29}$ and/or $R^{30}$ can link to $R^{32}$ and/or $R^{33}$ to form a cyclic structure selected from five-membered rings, six-membered rings, and fused five-membered and/or six-membered rings, wherein the cyclic structure is aromatic, alicyclic, heteroaromatic, or heteroalicyclic, and has zero, 1, 2, 3 or 4 non-hydrogen substituents and zero, 1, 2, or 3 heteroatoms.

As an example, $R^{29}$ and $R^{30}$ are selected from hydrogen, $C_1$-$C_{12}$ alkyl, $C_1$-$C_{12}$ alkoxy, $C_5$-$C_{20}$ aryl, $C_2$-$C_{12}$ alkoxyalkyl, $C_2$-$C_{12}$ alkoxycarbonyl, $C_6$-$C_{20}$ aryloxycarbonyl, and $C_6$-$C_{20}$ aryloxyalkyl, and $R^{32}$ and $R^{33}$ together form a $C_5$-$C_{12}$ cyclic structure that is alicyclic or heteroalicyclic and has zero, 1, 2, 3, 4, or more non-hydrogen substituents. As a further example, $R^{29}$ is hydrogen, $R^{30}$ is selected from hydrogen, $C_1$-$C_6$ alkyl, $C_5$-$C_{12}$ aryl, $C_2$-$C_6$ alkoxycarbonyl, $C_6$-$C_{12}$ aryloxycarbonyl, and $C_6$-$C_{12}$ aryloxyalkyl, and $R^{32}$ and $R^{33}$ together form a $C_5$-$C_8$ cyclic structure that is alicyclic or heteroalicyclic and has zero, 1, 2, or 3 non-hydrogen substituents.

The product of the catalyzed 1,4-hydride reduction of α,β-unsaturated cyclic ketones may therefore be a ketone comprising a chiral carbon moiety in the β-position relative to the carbonyl (i.e., a β-chiral ketone). Furthermore, the 1,4-hydride reductions of the invention may be characterized as enantioselective in that one enantiomer of the product is preferentially produced over the other enantiomer. The stereochemistry of the β-chiral ketone product is dependent upon the stereochemistry of the catalyst. Because of the enantioselectivity of the reaction, a product from the 1,4-hydride reductions of the invention involving a α,β-unsaturated cyclic ketone may be a β-chiral ketone with an enantiomeric excess of, for example, above 50%. As a further example, the enantiomeric excess of the product may be above 75%, as a further example above 85%, and as a still further example above 90%.

The Hydride Donor:

In the 1,4-hydride reduction reactions of the invention, any compound or composition that is capable of donating a hydride moiety may be used as a hydride source, as can mixtures of such compounds or compositions. Suitable hydride donors may be found in the pertinent chemical literature. A number of suitable hydride donors may be found, for example, in Smith et al. *March's Advanced Organic Chemistry, 5th Edition* (Wiley: New York, 2001). Non-limiting examples include $H_2$, alcohols (such as methanol, ethanol, n-propyl alcohol, and isopropyl alcohol), $PhSiH_3$, $NaBH_4$, and borohydride exchange resin.

In one embodiment, the hydride donor is a dihydropyridine. For example, the hydride donor may be selected from 1,4-dihydropyridines, 1,2-dihydropyridines, and 2,3-dihydropyridines. As a further example, the hydride donor may be a 1,4-dihydropyridine having the structure of formula (X)

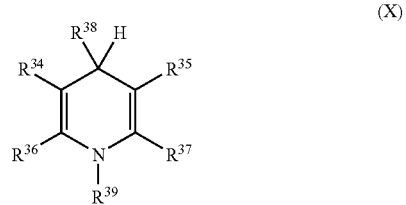

(X)

wherein $R^{34}$ and $R^{35}$ may be the same or different, and are selected from H and deactivating groups, $R^{36}$ and $R^{37}$ may be the same or different, and are selected from H and activating groups, and $R^{38}$ and $R^{39}$ may be the same or different, and are selected from H, $C_1$-$C_{24}$ alkyl, $C_2$-$C_{24}$ alkenyl, $C_2$-$C_{24}$ alkynyl, $C_5$-$C_{24}$ aryl, $C_6$-$C_{24}$ alkaryl, and $C_6$-$C_{24}$ aralkyl. Examples of activating groups include, by way of example and not limitation, $C_1$-$C_{24}$ alkyl, $C_2$-$C_{24}$ alkenyl, $C_2$-$C_{24}$ alkynyl, $C_5$-$C_{30}$ aryl, $C_6$-$C_{30}$ aralkyl, $C_6$-$C_{30}$ alkaryl, amino, $C_1$-$C_{24}$ amino, $C_1$-$C_{24}$ amido, hydroxyl, acyloxy, $C_1$-$C_{24}$ alkoxy, $C_2$-$C_{24}$ alkenyloxy, $C_2$-$C_{24}$ alkynyloxy, $C_5$-$C_{20}$ aryloxy, $C_2$-$C_{24}$ alkylamido, and $C_5$-$C_{20}$ arylamido. Examples of deactivating groups include, by way of example and not limitation, $C_1$-$C_{24}$ haloalkyl, $C_5$-$C_{24}$ haloaryl, $C_2$-$C_{24}$ acyl, $C_2$-$C_{24}$ alkoxycarbonyl, $C_6$-$C_{20}$ aryloxycarbonyl, carbamoyl, mono-substituted $C_1$-$C_{24}$ alkylcarbamoyl, di-substituted alkylcarbamoyl, mono-substituted arylcarbamoyl, halocarbonyl, nitro, cyano, azido, and formyl.

As a further example, in formula (X): $R^{34}$ is —$CO_2R^{40}$; $R^{35}$ is —$CO_2R^{41}$; $R^{36}$, $R^{37}$, $R^{40}$ and $R^{41}$ are independently chosen from $C_1$-$C_{24}$ alkyl, $C_5$-$C_{30}$ aryl, and $C_6$-$C_{30}$ aralkyl; and $R^{38}$ and $R^{39}$ are independently chosen from H and $C_1$-$C_{24}$ alkyl. As a still further example, in formula (X): $R^{34}$ is —$CO_2R^{40}$; $R^{35}$ is —$CO_2R^{41}$; $R^{36}$, $R^{37}$, $R^{40}$ and $R^{41}$ are independently selected from Me, Et, Pr, i-Pr, Bu, and t-Bu, Ph, and Bn; and $R^{38}$ and $R^{39}$ are H.

Any of the reactions herein, including both preparation and use of the imidazolidinone salt, can be carried out on a solid support, using solid phase synthesis techniques. Solid-phase synthesis enables synthesis and use of the imidazolidinone salt in combinatorial chemistry processes, wherein an array or "matrix" of reactions are conducted in parallel on a single solid support. In such a case, the imidazolidinone itself (or the anion with which the cationic imidazolidinone is associated) can be bound either directly or indirectly to the surface of a solid substrate, if indirectly, through a cleavable or noncleavable linker. For example, the imidazolidinone can be linked to the surface of a solid support through any of the substituents. Any solid support may be used. Typical support materials are those conventionally used in solid phase chemistry and which allow for chemical synthesis thereon. The only limitation upon the materials useful for constructing supports is that they must be compatible with the reaction conditions to which they are exposed. Suitable supports useful in practicing the methods of the invention are composed of materials that include, but are not limited to, organic and inorganic polymers (e.g., polyethylene, polypropylene, polystyrene, polytetrafluoroethylene), metal oxides (e.g., silica, alumina), mixed metal oxides, metal halides (e.g., magnesium chloride), minerals, quartz, zeolites, and the like. Other support materials will be apparent to those of skill in the art.

Process conditions: The catalytic reactions of the invention are typically carried out in water, an organic solvent, or an ionic liquid, i.e., in any solvent that allows retention and regeneration of the catalyst composition and removal of the reaction product following completion of the reaction. The reactions may be carried out in batch, semi-continuously or continuously, in air or an inert atmosphere, at autogenous pressure or higher, depending, for example, on the nature of the catalyst composition and reactants used. The reaction temperature will generally be, for example, in the range of about −100° C. to 100° C., and as a further example in the range of about −90° C. to 50° C. While lower temperatures, less than about 0° C., generally result in a higher yield and greater enantioselectivity, the reaction proceeds sufficiently rapidly for most purposes at ambient temperature, i.e., about 20° C. to 25° C.

The appropriate amount of catalyst (i.e., either an acid addition salt of the imidazolidinone, or a mixture of the imidazolidinone and an acid co-catalyst) is typically the range of about 0.1 mole % to 1 stoichiometric equivalent, more typically in the range of about 1 mol % to 1 stoichiometric equivalent. The molar ratio of the $\alpha,\beta$-unsaturated aldehyde or ketone to the hydride donor is generally in the range of about 100:1 to 1:100, preferably in the range of about 10:1 to 1:10. Industrially, the reaction may be scaled up to 10,000 gallons or more. It will be appreciated by those skilled in the art of catalysis that the aforementioned process conditions may vary depending on the particular reaction, the desired product, the equipment used, and the like. Generally, the reaction product is obtained after completion of the reaction, wherein an optional extraction and/or catalyst recovery step and/or drying is followed by concentration or distillation to give the crude product and purification, e.g., by chromatography, sublimation, precipitation, extraction, crystallization with optional seeding and/or co-crystallization aids.

Hydride Donor/Catalyst Combination:

Another embodiment of the invention provides for a combination of a hydride donor and an imidazolidinone catalyst, generally in an admixture in a single composition. The composition is intended for use in carrying out the methods of the invention, i.e., enantioselective 1,4-hydride reduction of $\alpha,\beta$-unsaturated carbonyl-containing compounds. The composition may comprise one or more of any of the catalysts described herein, and may further comprise one or more of any of the hydride donors described herein. For example, the composition may comprise a catalyst of formula (IIA) or (IIB) and a hydride donor or formula (X). As a further example, the composition may comprise a catalyst of formula (VIA) or (VIIB) and a hydride donor of formula (XI).

The compositions of the invention may further include one or more acids capable of forming an acid addition salt with the catalyst. Any of the acids described herein may be used in the composition. The composition may be prepared, for example, using an acid addition salt of the catalyst. Alternatively, the composition may be prepared using the neutral form of the catalyst, and an acid may be added to the composition in order to form in situ an acid addition salt of the catalyst. When the composition is used to carry out an enantioselective 1,4-hydride reduction of $\alpha,\beta$-unsaturated carbonyls, the acid may be added to the reaction mixture separately from the composition, such that the composition per se does not contain an acid.

The molar ratio of catalyst to hydride donor can be, for example, between 1:30 and 1:1. As a further example, the catalyst-to-hydride donor ratio can be between 1:15 and 1:6; and as a still further example, the ratio can be between 1:12 and 1:6.5.

The compositions of the invention may additionally contain one or more components selected from solvents, pH buffers, stabilizers, inert solid supports and other additives that are discussed herein or will be apparent to one of skill in the art. As an example, suitable solvents include, without limitation, hydrocarbons such as pentane, and hexane, ethers such as tetrahydrofuran, dioxane, diethyl ether, and diphenyl ether, alcohols such as methanol, ethanol, propanol, isopropanol, butanol, and pentanol, acetonitrile, dimethylformamide, chlorinated hydrocarbons such as dichloromethane, chloroform, and carbon tetrachloride, fluorinated hydrocarbons, aromatics such as benzene, toluene, xylene and trimethylbenzene, carbonyl compounds such as formaldehyde, acetone, butanone, ethyl acetate, and phenyl acetate. Suitable stabilizers include, without limitation, antioxidants such as butylated hydroxytoluene and the like, and sequestering agents such as ethylenediaminetetraacetic acid and the like.

It is to be appreciated that, in selecting the components of the composition, the identities of the components and their molar ratio will depend upon the intended application. For example, selection of the most effective combination of components may be influenced by the identity of the substrate (i.e., the $\alpha,\beta$-unsaturated carbonyl-containing compound) as well as desired reaction conditions (e.g., temperature or reaction time). The examples provided herein may be used as guidance in selection of maximally effective components and molar ratios.

It is to be understood that while the invention has been described in conjunction with specific embodiments thereof, that the description above as well as the examples that follow are intended to illustrate and not limit the scope of the invention. Other aspects, advantages and modifications within the scope of the invention will be apparent to those skilled in the art to which the invention pertains.

All patents, patent applications, journal articles and other reference cited herein are incorporated by reference in their entireties.

Experimental

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

Commercial reagents were purified prior to use following the guidelines of Perrin et al. (1996), *Purification of Laboratory Chemicals*, Fourth Edition (Oxford, Butterworth-Heinemann). Organic solutions were concentrated under reduced pressure on a Büchi rotary evaporator. Methylene chloride was distilled from calcium hydride prior to use. Tetrahydrofuran was distilled from sodium benzophenone ketyl prior to use. Chloroform was distilled from calcium sulfate and potassium carbonate and passed through an alumina plug prior to use. Non-aqueous reagents were transferred under nitrogen via syringe or cannula and purified according to the method of Pangborn et al. (1996) *Organometallics* 15:15182. Chromatographic purification of products was accomplished using forced-flow chromatography on ICN 60 32-64 mesh silica gel 63 and Iatrobeads® according to the method of Still et al. (1978), *J. Org. Chem.* 43:2923. Thin-layer chromatography (TLC) was performed on EM Reagents 0.25 mm silica gel 60-F plates. Visualization of the developed chromatogram was performed by fluorescence quenching, anisaldehyde stain, potassium permanganate stain or dinitrophenylhydrazine stain.

$^1$H and $^{13}$C NMR spectra were recorded on Varian Mercury 300 spectrometers (300 MHz and 75 MHz respectively) as noted, and are internally referenced to residual protio solvent signals. Data for $^1$H NMR are reported as follows: chemical shift (δppm), multiplicity (s=singlet, d=doublet, t=triplet, q=quartet, m=multiplet, br=broad), coupling constant (Hz), integration and assignment. Data for $^{13}$C NMR are reported in terms of chemical shift (δppm). IR spectra were recorded on a Perkin Elmer Paragon 1000 spectrometer and are reported in terms of frequency of absorption (cm$^{-1}$). Mass spectra were obtained either from the UC Irvine Mass Spectral facility or from the Caltech Mass Spectroscopy facility by electron ionization, chemical ionization, of fast atom/ion bombardment techniques. Gas liquid chromatography (GLC) was performed on Hewlett-Packard 6850 and 6890 Series gas chromatographs equipped with a splitmode capillary injection system and flame ionization detectors using a Bodman Chiraldex β-DM (30 m×0.25 mm), a Bodman ChiraldexΓ-TA (30 m×0.25 mm) or a Hydrodex-B-TBDAc (50 m×0.25 mm) column as noted. High performance liquid chromatography (HPLC) was performed on Hewlett-Packard 1100 Series chromatographs using either Chiralcel OD-H column (25 cm) and OD-H guard (5 cm) or Chiralpak AD column (0.46×25 cm) and AD guard (0.46×5 cm). Optical rotations were taken using a Jasco P-1010 polarimeter (WI lamp, 589 nm, 25° C.). Optical rotations were measured on a Jasco P-1010 polarimeter, and [α]$_D$ values are reported in 10$^{-1}$ dg cm$^2$ g$^{-1}$; concentration (c) is in g/100 ml.

The following α,β-unsaturated aldehydes have already been described in the literature: (E)-3-phenylbut-2-enal (Gandhi, et al. (1957), *J. Indian Chem. Soc.* 34:509); (E)-3-phenylpent-2-enal, (Schreiber et al. (1974) *J. Agr. Food Chem.* 22:269); and (E)-methyl-3-formyl-2-methylacrylate (Ishida, et al. (1978), *Bull. Chem. Soc. Jpn.* 51:2077).

The following α,β-unsaturated cyclic enones are commercially available from Aldrich: 3-methyl-2-cyclopenten-1-one and isophorone (3,5,5-trimethylcyclohex-2-enone). The following α,β-unsaturated cyclic enones have already been described in the literature: 3-hexylcyclopent-2-enone, 3-cyclohexylcyclopent-2-enone (Collins et al. (1990), *J. Org. Chem.* 55:3395), 3-tert-butylcyclopent-2-enone (Ponaras et al. (1988), *J. Org. Chem.* 53:1110; and Garbisch et al. (1969), *J. Am. Chem. Soc.* 91:6785), 3-phenylcyclopent-2-enone (Jurkauskas et al. (2003), *Org. Lett.* 5:2417), 3-benzylcyclopent-2-enone (Moritani et al. (2000), *J. Am. Chem. Soc.* 122:6797), 3-(benzyloxymethyl)cyclopent-2-enone (Dauben et al. (1990), *J. Org. Chem.* 55:3075), methyl 3-oxocyclopent-1-enecarboxylate, 3-acetylcyclopent-2-enone (Yu et al. (2003), *J. Am. Chem. Soc.* 125:3232; and Catino et al. (2004), *J. Am. Chem. Soc.* 126:13622), 3-butylcyclohex-2-enone (Mudryk et al. (1993), *J. Am. Chem. Soc.* 115:385), 3-cyclohexylcyclohex-2-one (Snider et al. (1980), *J. Am. Chem. Soc.* 102:872).

EXAMPLE 1

This example describes the synthesis of a catalyst used in the method of the invention in two steps from phenylalanine methyl ester, according to the following scheme:

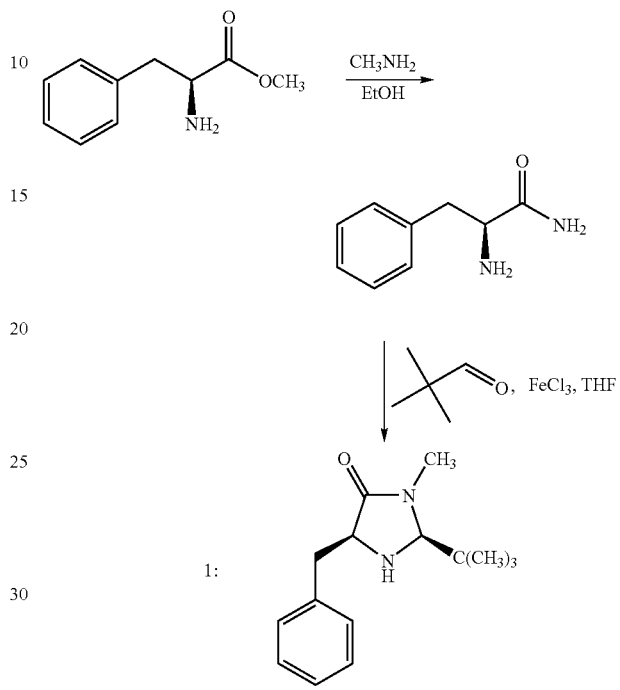

Preparation of the hydrochloride salt of (2S,5S)-5-benzyl-2-tert-butyl-3-methyllimidazolidin-4-one (1): To a solution of ethanolic MeNH$_2$ (8.0 M, 50 ml) was added (S)-phenylalanine methyl ester (23.0 g, 130 mmol). The resulting solution was stirred at room temperature until the amino ester was judged to be consumed by TLC analysis. The resulting solution was then concentrated to provide (S)-phenylalanine N-methyl amide (18 g, 82% yield) as a white solid. To a flask containing (S)-phenylalanine N-methyl amide (8.9 g, 50 mmol) was added THF (100 ml), trimethylacetaldehyde (5.4 g, 50 mmol), FeCl$_3$ (1.7 g, 10 mmol) and 4 Å MS (5.0 g). The resulting mixture was stirred at room temperature for 36 h, then washed with H$_2$O (3×100 mL). The combined organics were concentrated and the resulting residue was treated with HCl (27 mL, 1N in ether). The resulting heterogeneous mixture was filtered to removed the undesired trans isomer•HCl salt and the resulting solution was concentrated. The residue was recrystallized (9:1 pentane/CH$_2$Cl$_2$) to provide the product (1) as a crystalline solid (2.88 g, 23% yield, >99% ee). IR (film) 3343, 2958, 1605, 1028 cm$^{-1}$; $^1$H NMR (300 MHz, CDCl$_3$) δ 7.31-7.17 (m, 5H, ArH), 4.04 (s, 1H, NCHN), 3.72-3.65 (m, 1H, CHCH$_2$), 3.13 (dd, J=4.1, 13.7 Hz, 1H, CH$_2$), 2.92 (dd, J=7.7, 13.7 Hz, 1H, CH$_2$), 2.90 (s, 3H, NCH$_3$), 0.82 (s, 9H, C(CH$_3$)$_3$); $^{13}$C NMR (75 MHz, CDCl$_3$) δ 175.3, 138.0, 129.8, 128.7, 126.8, 82.7, 77.8, 77.4, 76.9, 59.7, 38.6, 35.4, 31.0, 25.7; [α]$_D$=−39.6 (c=1.0, CHCl$_3$). The enantiomeric ratio was determined by HPLC using a Chiralpak OD-H and OD guard column (3.0% i-PrOH/hexanes, 1 mL/min); (5S) isomer t$_r$=16.7 min, (5R) isomer t$_r$=20.1 min.

The trans (2R,5S) isomer of catalyst (1) can be converted to the desired cis (2S,5S) isomer as follows: A solution of trans-(2R,5S)-5-benzyl-2-tert-butyl-3-methylimidazolidin-4-one•HCl salt (6.0 g, 27.9 mmol) in Et$_2$O (100 mL) was washed with saturated aqueous NaHCO$_3$ (100 mL) before the organics were separated and concentrated. To a flask containing the resulting residue was added THF (50 ml) and FeCl$_3$ (0.95 g, 5.6 mmol). The resulting solution was maintained at room temperature for 14 h, then washed with H$_2$O (3×50 mL). The combined organics were concentrated and the resulting residue was treated with HCl (13 mL, 1N in ether). The resulting heterogeneous mixture was filtered to removed the undesired trans isomer.HCl salt and the resulting solution was concentrated. The residue was recrystallized (9:1 pentane/CH$_2$Cl$_2$) to provide the product as a crystalline solid (1.65 g, 22% yield, >99% ee).

It will be appreciated that the foregoing method can be readily adapted for the synthesis of analogous catalysts, e.g., imidazolidinones encompassed by formulae (IIA) and (IIB), or (VIIA) and (VIIB), by using appropriately substituted reactants as starting materials.

EXAMPLE 2

Preparation of (E)-3-cyclohexylbut-2-en-1-ol: To a 0° C. solution of (E)-ethyl 3-cyclohexylbut-2-enoate (Appella et al. (1999), *J. Am. Chem. Soc.* 121:9473) (1 g, 5.09 mmol) in dry Et$_2$O (10 mL) was added a solution of lithium aluminum hydride (5.10 mL, 5.10 mmol, 1 M in Et$_2$O). After 5 minutes, the reaction mixture was neutralized by dropwise addition of THF solution followed by addition of a saturated solution of potassium sodium tartrate. The reaction mixture was stirred for 25 minutes, and then diluted with Et$_2$O. The organic layer was separated and washed with water, dried over Na$_2$SO$_4$ and concentrated in vacuo to afford (E)-3-cyclohexylbut-2-en-1-ol as a colorless oil which was used directly in the following reaction.

EXAMPLE 3

Preparation of (E)-3-cyclohexylbut-2-enal: To a solution of (E)-3-cyclohexylbut-2-enol (700 mg, 4.54 mmol) in dichloromethane (11 mL), cooled to 0° C., was added Dess-Martin periodinane (2.11 g, 4.99 mmol). The resulting suspension was warmed to 23° C. and stirred for approximately 30 minutes until the reaction was judged to be complete by TLC. The reaction mixture was poured into 50 mL of saturated aqueous NaHCO$_3$ containing Na$_2$S$_2$O$_3$ (1 g). This mixture was stirred vigorously until both layers became clear. The aqueous layer was extracted with CH$_2$Cl$_2$ (2×) and the combined organic layers were dried over MgSO$_4$, filtered and concentrated in vacuo. The residue was purified by flash chromatography (25% EtOAc/hexanes) to afford the title compound as a colorless oil (350 mg, 51% yield) that was a 5.2:1 mixture of E:Z isomers. Major isomer: IR (film) 2929, 2854, 1729, 1674, 1640, 1450, 1383, 1198, 1164, 894, 850, 522 cm$^{-1}$; $^1$H NMR (300 MHz, CDCl$_3$) δ 10.05 (d, 1H, J=7.9 Hz CHO), 5.90 (dq, 1H, J=1.1, 7.9 Hz, C=CH), 2.18 (d, 3H, J=1.3 Hz, CH$_3$), 2.09-2.02 (m, 1H, CH$_2$CHCH$_2$), 1.87-1.70 (m, 5H), 1.40 (m, 5H); $^{13}$C NMR (75 MHz, CDCl$_3$) δ 191.9, 168.8, 125.8, 48.4, 31.4, 31.2, 26.3, 26.1, 26.0, 16.1; HRMS (EI$^+$) exact mass calculated for [M]$^+$ (C$_{10}$H$_{16}$O) requires m/z 152.1201, found m/z 152.1205.

EXAMPLE 4

Preparation of (E)-ethyl 3-cyclohexylpent-2-enoate: To 90 mL of EtOH, cooled to 0° C. in an ice bath, was added sodium metal (1.64 g, 71.3 mmol). Once the metal had completely dissolved, triethyl phosphonoacetate (15.9 g, 14.1 mL, 71.3 mmol) was added via syringe. The resulting solution was warmed to room temperature and stirred for 10 minutes. Cyclohexyl ethyl ketone (9.44 g, 9.20 mL, 67.3 mmol) was added and the solution stirred for 15 h at room temperature. The reaction was quenched in 100 mL ice water slurry. The aqueous layer was extracted with 200 mL of Et$_2$O (3×). The combined organic layers were washed with 400 mL of brine, dried over Na$_2$SO$_4$, filtered and concentrated in vacuo. The product was purified by flash chromatography (1% Et$_2$O/pentane) to provide a clear oil (2.5 g, 18% yield) that was a 3:1 mixture of E:Z isomers. Major isomer: IR (film) 2977, 2929, 2854, 2360, 2341, 1716, 1638, 1448, 1203, 1147, 1042, 862, 750 cm$^{-1}$; $^1$H NMR (300 MHz, CDCl$_3$) δ 5.58 (s, 1H, C=CH), 4.15 (q, 2H, J=4.1 Hz, OCH$_2$CH$_3$), 2.58 (q, 2H, J=7.4 Hz, CH$_2$CH$_3$), 1.81-1.62 (m, 5H), 1.35-1.11 (m, 9H), 1.06 (t, 3H, J=2.2 Hz, CH$_2$CH$_3$); $^{13}$C NMR (75 MHz, CDCl$_3$) δ 171.3, 31.2, 26.9, 26.8, 26.6, 26.3, 25.3, 14.5, 13.8; HRMS (EI$^+$) exact mass calculated for [M] (C$_{13}$H$_{22}$O$_2$) requires m/z 210.1620, found m/z 210.1628.

EXAMPLE 5

Preparation of (E)-3-cyclohexylpent-2-enol: To a solution of (E)-ethyl 3-cyclohexylpent-2-enoate (2.3 g, 10.9 mmol) in Et$_2$O (22 mL), was added lithium aluminum hydride (1.0 M in Et$_2$O, 10.9 mL, 10.9 mmol) dropwise. After 5 minutes, the reaction mixture was slowly quenched with 1 mL of MeOH and poured into 100 mL of a saturated solution of potassium sodium tartrate. The aqueous layer was extracted with 100 mL Et$_2$O (3×). The combined organics were dried over Na$_2$SO$_4$, filtered and concentrated. The product was purified by flash chromatography (10% EtOAc/hexanes) to provide a clear oil (1.59 g, 87% yield) that was a 3:1 mixture of E:Z isomers. Major isomer: IR (film) 3421, 2929, 2854, 1732, 1684, 1635, 1449, 1235, 1164, 864, 749 cm$^{-1}$; $^1$H NMR (300 MHz, CDCl$_3$) δ 5.33 (t, 1H, J=6.7 Hz, CHCH$_2$OH), 4.17 (d, 2H, J=6.9 Hz, CH$_2$OH), 2.07 (q, 2H, J=7.4 Hz, CH$_2$CH$_3$), 1.99 to 1.63 (m, 6H), 1.48-1.08 (m, 6H), 0.97 (t, 3H, J=7.4 Hz, CH$_2$CH$_3$); $^{13}$C NMR (75 MHz, CDCl$_3$) δ 151.1, 121.2, 59.4, 44.8, 32.6, 31.6, 26.9, 26.7, 26.4, 23.1, 14.7; HRMS (EI$^+$) exact mass calculated for [M]$^+$ (C$_{11}$H$_{20}$O) requires m/z 168.1514, found m/z 168.1520.

EXAMPLE 6

Preparation of (E)-3-cyclohexylpent-2-enal: To a solution of (E)-3-cyclohexylpent-2-enol (1.50 g, 8.91 mmol) in dichloromethane (45 mL), cooled to 0° C., was added Dess-Martin periodinane (9.7 g, 22.9 mmol). The resulting suspension was warmed to room temperature and stirred for approximately 2 h until the reaction was judged to be complete by TLC. The reaction was poured into 100 mL of saturated aqueous NaHCO$_3$ containing Na$_2$S$_2$O$_3$ (3 g). This mixture was stirred vigorously until both layers became clear. The aqueous layer was extracted with CH$_2$Cl$_2$ (2×) and the combined organic layers were dried over MgSO$_4$, filtered and concentrated in vacuo. The residue was purified by flash chromatography (5% Et$_2$O/pentane) to afford the title compound (1 g, 68% yield) as a colorless oil that was a 3:1 mixture of E:Z isomers. Major isomer: IR (film) 2927, 2746, 1668, 1622, 1450, 1189, 1124, 860 cm$^{-1}$; $^1$H NMR (300 MHz, CDCl$_3$) δ 10.04 (d, 1H, J=8.24 Hz, CHO), 5.83 (d, 1H, J=8.24 Hz, C=CH), 2.61 (q, 2H, J=7.4 Hz, CH$_2$CH$_3$), 2.07 (tt, 1H, J=2.6, 11.0 Hz, CH$_2$CHCH$_2$), 1.88-1.71 (m, 5H), 1.41-1.15 (m, 8H); $^{13}$C NMR (75 MHz, CDCl$_3$) δ 191.8, 175.2, 124.9, 46.2, 31.9, 26.5, 26.3, 26.0, 25.9, 24.2, 15.4; HRMS (EI+) exact mass calculated for [M]+ ($C_{11}H_{18}O$) requires m/z 166.1358, found m/z 166.1355.

EXAMPLE 7

Preparation of (E)-ethyl 4-[tris-(1-methylethyl)silyloxy]-3-methylbut-2-enoate: To a suspension of sodium hydride (60% dispersion in mineral oil, 1.58 g, 62.6 mmol) in dry toluene (500 mL) at 0° C., was added, dropwise, triethyl phosphonoacetate (12.4 mL, 62.6 mmol) under an atmosphere of argon. After 30 minutes, 1-[tris-(1-methylethyl) silyloxy]-pentanone (12 g, 52.2 mmol) was diluted into toluene (25 mL) and added to the reaction mixture, which was then allowed to warm to room temperature over a period of 2 h. The resulting mixture was washed with water, dried over $MgSO_4$ and concentrated in vacuo. The residue was purified by flash chromatography (3% $Et_2O$/pentane) to afford (E)-ethyl 4-[tris-(1-methylethyl)silyloxy]-3-methylbut-2-enoate as a colorless oil (10.5 g, 67% yield). Major isomer: IR (film) 2945, 2868, 1716, 1663, 1223, 1154, 1114 cm$^{-1}$; $^1$H NMR (300 MHz, $CDCl_3$) δ 6.07 (bs, 1H, CH), 4.21 (s, 2H, $CH_2$OTIPS), 4.17 (q, 2H, J=6.9 Hz, $CH_3CH_2O$), 2.06 (s, 3H, $CCH_3$), 1.29 (t, 3H, J=7.8 Hz, $CH_3CH_2O$), 1.09 (m, 21H, TIPSO); $^{13}$C NMR (75 MHz, $CDCl_3$) δ 167.0, 157.0, 113.2, 67.2, 59.4, 17.9, 15.3, 14.3, 11.9; HRMS (EI+) exact mass calculated for [M]+ ($C_{16}H_{32}O_3Si$) requires m/z 300.2121, found m/z 300.2125.

EXAMPLE 8

Preparation of (E)-3-[tris-(1-methylethyl)silyloxy]but-2-en-1-ol: To a 0° C. solution of (E)-ethyl 4-[tris-(1-methylethyl)silyloxy]-3-methylbut-2-enoate (5 g, 17.6 mmol) in dry $Et_2O$ was added a solution of lithium aluminum hydride (17.6 mL, 17.6 mmol, 1 M in $Et_2O$). After 30 minutes, the reaction mixture was neutralized by dropwise addition of THF followed by addition of a saturated solution of potassium sodium tartrate. The reaction mixture was stirred overnight and then diluted with $Et_2O$. The organic layer was separated and washed with water, dried over $MgSO_4$ and concentrated in vacuo to afford (E)-3-[tris-(1-methylethyl) silyloxy]but-2-en-1-ol as a colorless oil which was used directly into the next reaction.

(E)-3-[tris-(1-methylethyl)silyloxymethyl]but-2-enal: To a room temperature solution of (E)-3-[tris-(1-methylethyl) silyloxy]but-2-en-1-ol (crude from the previous step, assumed 17.6 mmol) in dichloromethane (100 mL) was added Dess-Martin periodinane (9.7 g, 22.9 mmol). The resulting suspension was stirred for 60 minutes, until the reaction was judged to be complete by TLC. The reaction mixture was diluted with $Et_2O$ and a saturated aqueous solution of $NaHCO_3$ containing $Na_2S_2O_3$ was added. This mixture was stirred vigorously until both layers became clear. The aqueous layer was extracted with $CH_2Cl_2$ (2×) and the combined organic layers were dried over $MgSO_4$, filtered and concentrated in vacuo. The residue was purified by flash chromatography (5% $Et_2O$/pentane) to afford the title compound as a colorless oil (3.69 g, 82% yield). IR (film) 2944, 2867, 1681, 1464, 1384, 1123 cm$^{-1}$; $^1$H NMR (300 MHz, $CDCl_3$) δ 10.09 (d, 1H, J=8.3 Hz, CHO), 6.28 (dd, 1H, J=1.5, 8.4 Hz, CH), 4.28 (d, 2H, J=0.9 Hz, $CH_2$OTIPS), 2.09 (d, 3H, J=0.6 Hz, $CH_3C$), 1.1 to 1.0 (m, 21H, TIPSO); $^{13}$C NMR 75 MHz, $CDCl_3$) δ 191.2, 161.6, 124.1, 67.0, 18.0, 14.1, 11.9; HRMS (EI+) exact mass calculated for [M]+ ($C_{14}H_{28}O_2Si$) requires m/z 256.1859, found m/z 256.1862.

EXAMPLE 9

TABLE 1

Effect of Catalyst and Solvent on Organocatalytic Hydride Reduction[a]

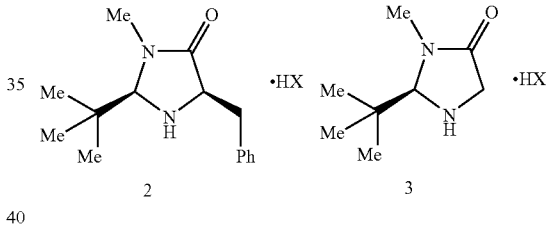

| Entry | Catalyst | HX | Solvent | Time [h] | Conversion [%][b] | ee [%][c] |
|---|---|---|---|---|---|---|
| 1 | L-proline | TFA | Toluene | 5 | 47 | 15 |
| 2 | 2 | TFA | Toluene | 1 | 96 | 75 |
| 3 | 3 | TFA | Toluene | 1 | 95 | 88 |
| 4 | 2 | HCl | Toluene | 8 | 70 | 81 |
| 5 | 3 | HCl | Toluene | 31 | 19 | 87 |
| 6 | 3 | TFA | CHCl$_3$ | 1 | 99 | 85 |
| 7 | 3 | TFA | CHCl$_3$ | 24 | 90[d] | 93 |
| 8 | 3 | TCA | CHCl$_3$ | 23 | 91[d] | 93 |

[a]Reaction conditions: 20 mol % catalyst · HX, solvent, 4° C. For reaction procedures, see Examples 10-16.
[b]Conversion determined by GLC analysis.
[c]Enantiomeric excess determined by chiral GLC analysis (Bodman Γ-TA).
[d]At −30° C.

Examples 10-16

General procedure for the enantioselective hydrogenation of enals: A colorless solution of (E)-3-phenylbut-2-enal (140 mg, 1 mmol) dissolved in 5 mL of chloroform (0.2 M) was cooled to −30° C. in a dry ice/acetone bath. To this solution was added the trichloroacetic acid salt of (R)-2-tert-butyl-3-methylimidazolidin-4-one (64 mg, 0.2 mmol) and Hantzsch ester (304 mg, 1.2 mmol). The resulting yellow suspension was stirred at −30° C. until the reaction was determined to be complete by TLC, by which time the mixture was a light yellow homogeneous solution. Workup procedure A: The reaction mixture was then diluted with $Et_2O$ and passed though a short pad of silica gel. The resulting solution was concentrated in vacuo and purified by flash chromatography (solvent noted) to provide the title compounds. Workup procedure B: The cold reaction mixture was poured into a 10% HCl solution and diluted with $Et_2O$. The organic layer was washed 4 times with 10% HCl solution and once with a saturated aqueous solution of $NaHCO_3$. The resulting solution was dried over $MgSO_4$ and concentrated in vacuo. The residue was purified by flash chromatography (solvent noted) to provide the title compounds.

TABLE 2

Effect of Substituents on Organocatalytic Hydride Reduction of Aldehydes.[a]

R₁R₂C=CH-CHO + Hantzsch ester (EtO₂C-substituted dihydropyridine with CH₃ groups) + catalyst (Me-N, t-Bu imidazolidinone·TFA), CHCl₃, −30° C. → R₁R₂CH-CH₂-CHO product

| Entry | E:Z (substrate) | Product | Time [h] | Yield [%] | ee [%][b] |
|---|---|---|---|---|---|
| 1 | >20:1 | (S)-3-phenylbutanal | 23 | 91 | 93[c] |
| 2 | >20:1 | (S)-3-phenylbutanal | 48 | 79 | 94[c,d] |
| 3 | >20:1 | (S)-3-phenylpentanal | 16 | 74 | 94 |
| 4 | >20:1 | 3-(3,4-dichlorophenyl)butanal | 16 | 92 | 97 |
| 5 | 5:1 | (S)-3-cyclohexylbutanal | 10 | 91 | 96[c] |
| 6 | 3:1 | 3-cyclohexylpentanal | 23 | 95 | 91[d] |
| 7 | >20:1 | methyl ester aldehyde | 26 | 83[e] | 91[f] |
| 8 | >20:1 | TIPSO-CH₂-CH(CH₃)-CH₂-CHO | 72 | 74 | 90 |
| 9 | >20:1 | (CH₃)₃C-CH(CH₃)-CH₂-CHO | 0.5 | 95[e] | 97[g] |

[a]Using 20 mol % catalyst unless otherwise specified.
[b]Enantiomeric excess determined by chiral GLC analysis.
[c]Performed at −45° C.
[d]Using 10 mol % catalyst.
[e]Yield determined by NMR.
[f]Performed at −50° C.
[g]Using 5 mol % catalyst at 23° C.

EXAMPLE 10

Preparation of (S)-3-phenylbutanal (Table 2, entry 1). Prepared according to the general procedure from (E)-3-phenylbut-2-enal (140 mg, 1 mmol) for 23 h, using workup procedure A to provide the title compound as a colorless oil (127 mg, 91% yield, 93% ee) after purification by flash chromatography on Iatrobeads® (20% Et₂O/pentane). The physical data were identical in all respects to those previously reported (Bull et al. (2003), *Org. Biomol. Chem.* 1:2886). The enantiomeric ratio was determined by GLC using a Bodman Chiraldex β-DM (30 m×0.25 mm) column (90° C. isotherm, 1 mL/min); (R) isomer $t_r$=38.6 min and (S) isomer $t_r$=39.5 min. $[\alpha]_D^{22}$=+32.90 (c=1.00, EtOH).

EXAMPLE 11

Preparation of (S)-3-phenylpentanal (Table 2, entry 3). Prepared according to the general procedure from (E)-3-phenylpent-2-enal (160 mg, 1 mmol) for 16 h, using workup procedure A to provide the title compound as a colorless oil (119 mg, 74% yield, 94% ee) after purification by flash chromatography on Iatrobeads® (10% Et₂O/pentane). The physical data were identical in all respects to those previously reported (a rotation of +2.1° for a product that was 15% ee has been reported; see Berlan et al. (1986), *Tetrahedron* 42:4757). The enantiomeric ratio was determined by GLC using a Bodman Chiraldex β-DM (30 m×0.25 mm) column (95° C. isotherm, 1 L/min); (R) isomer $t_r$=42.8 min and (S) isomer $t_r$=43.9 min. $[\alpha]_D^{22}$=+20.1° (c=1.00, EtOH).

EXAMPLE 12

Preparation of (S)-3-cyclohexylbutanal (Table 2, entry 5). Prepared according to the general procedure from (E)-3-cyclohexylbut-2-enal (154 mg, 1 mmol) for 22 h, using workup procedure A to provide the title compound as a colorless oil (45.1 mg, 91% yield, 96% ee) after purification by flash chromatography on silica gel (10% Et₂O/hexane). The physical data were identical in all respects to those previously reported (a rotation of +7.4° for a product that was 74% ee was reported; see Tanaka el at. (2001), *J. Org. Chem.* 66:8177). The enantiomeric ratio was determined by GLC using a Bodman Chiraldex β-DM (30 m×0.25 mm) column (80° C. isotherm, 1 mL/min); (R) isomer $t_r$=70.6 min and (S) isomer $t_r$=71.3 min. $[\alpha]_D^{22}$=+8.30 (c=1.00, EtOH).

EXAMPLE 13

Preparation of (S)-3-cyclohexylpentanal (Table 2, entry 6). Prepared according to the general procedure from (E)-3-cyclohexylpent-2-enal (250 mg, 1.50 mmol) for 24 h, using workup procedure A to provide the title compound as a colorless oil (240.8 mg, 95% yield, 91% ee) after purification by flash chromatography on silica gel (10% Et$_2$O/pentane). The enantiomeric ratio was determined by GLC using a Hydrodex-B-TBDAc (50 m×0.25 mm) column (90° C. isotherm, 1 mL/min); (R) isomer t$_r$=35.2 min and (S) isomer t$_r$=37.9 min. IR (film) 2927, 2854, 1732, 1708, 1449, 1412, 1381, 1286, 1164, 954, 892 cm$^{-1}$; $^1$H NMR (300 MHz, CDCl$_3$) δ 9.79 (t, 1H, J=2.4.3 Hz, CHO), 2.44, (ddd, 1H, J=2.1, 5.8, 16.4 Hz, CH), 2.28 (ddd, 1H, J=2.7, 7.2, 16.2 Hz, CH), 1.82 to 1.61 (m, 5H), 1.47 to 0.99 (m, 12H); $^{13}$C NMR (75 MHz, CDCl$_3$) 203.9, 45.7, 40.3, 39.9, 30.4, 29.2, 26.74, 26.69, 26.67, 24.3, 11.8; HRMS (EI$^+$) exact mass calculated for [M]$^+$ (C$_{11}$H$_{20}$O) requires m/z 168.1514, found m/z 168.1522; [α]$_D^{22}$=+6.2° (c=1.03, CHCl$_3$).

EXAMPLE 14

Preparation of (S)-methyl 2-methyl-4-oxobutanoate (Table 2, entry 7). Prepared according to the general procedure from (E)-methyl 3-formyl-2-methylacrylate (100 mg, 0.781 mmol) for 26 h to provide the title compound (83% yield, 91% ee). Yield was determined via $^1$H NMR by comparison with an internal standard (BnOMe). The physical data were identical in all respects to those previously reported (a rotation of +0.580 for a product that was 10% ee was reported; see Kollar et al. (1987), *J. Organomet. Chem.* 330:305). The enantiomeric ratio was determined by GLC using a Bodman Chiraldex β-TA (30 m×0.25 mm) column (100° C. isotherm, 1 mL/min); (S) isomer t$_r$=6.7 min and (R) isomer t$_r$=7.7 min. [α]$_D^{22}$=+1.4° (c=1.15, CHCl$_3$).

EXAMPLE 15

Preparation of (S)-3-[tris-(1-methylethyl)silyloxymethyl] butanal (Table 2, entry 8). Prepared according to the general procedure from (E)-3-[tris-(1-methylethyl)silyloxymethyl] but-2-enal (245 mg, 1 mmol) for 72 h, using workup procedure A to provide the title compound as a colorless oil (190 mg, 74% yield, 90% ee) after purification by flash chromatography on Iatrobeads® 10% Et$_2$O/pentane). The enantiomeric ratio was determined by HPLC (the aldehyde was reduced and protected using BzCl) on Chiralcel® OD-H (0.46 mm×25 cm) isocratic 5% EtOH/Hexanes, 1 mL/min, 25° C.; (S) isomer t$_r$=19.2 min and (R) isomer t$_r$=22.2 min. IR (film) 2944, 2867, 2716, 1728, 1464, 1385, 1101 cm$^{-1}$; $^1$H NMR (300 MHz, CDCl3) δ 9.80 (t, 1H J=2.4 Hz, CHO), 3.66 (dd, 1H, J=5.1, 9.9 Hz, TIPSOCH), 3.47 (dd, 1H, J=6.9, 9.6 Hz, TIPSOCH), 2.58 (m, 1H, CHCHO), 2.28 (m, 2H, MeCHCH), 1.06 (m, 21H, TIPSO), 0.97 (d, J=6.9 Hz, CH$_3$); $^{13}$C NMR (75 MHz, CDCl3) δ 202.7, 68.0, 48.2, 31.6, 17.9, 16.7, 11.9; HRMS (EI$^+$) exact mass calculated for [M-H]$^+$ (C$_{14}$H$_{29}$O$_2$Si) requires m/z 257.1930 found m/z 257.1937; [α]$_D^{22}$=-2.7° (c=1.07, CHCl$_3$).

EXAMPLE 16

Preparation of (S)-3,4,4-trimethylpentanal (Table 2, entry 9). Prepared according to the general procedure, at room temperature, from (E)-3,4,4-trimethylpent-2-enal (70 mg, 0.56 mmol) for 5 minutes to provide the title compound (95% yield, 97% ee). Yield was determined using $^1$H NMR by comparison with an internal standard (BnOMe). The physical data were identical in all respects to those previously reported (a rotation of +3.4° for a product that was 16% ee was reported; see Berlan et al. (1986), *Tetrahedron* 42:4757). The enantiomeric ratio was determined by GLC using a Bodman Chrialdex β-DM (30 m×0.25 mm) column (60° C. isotherm, 1 mL/min); (R) isomer t$_r$=19.29 min and (S) isomer t$_r$=20.32 min. [α]$_D^{22}$=+29.3° (c=1.00, CHCl$_3$).

EXAMPLE 17

TABLE 3

Additional Solvent Screening Data for Organocatalytic Hydride Reduction of Aldehydes[a]

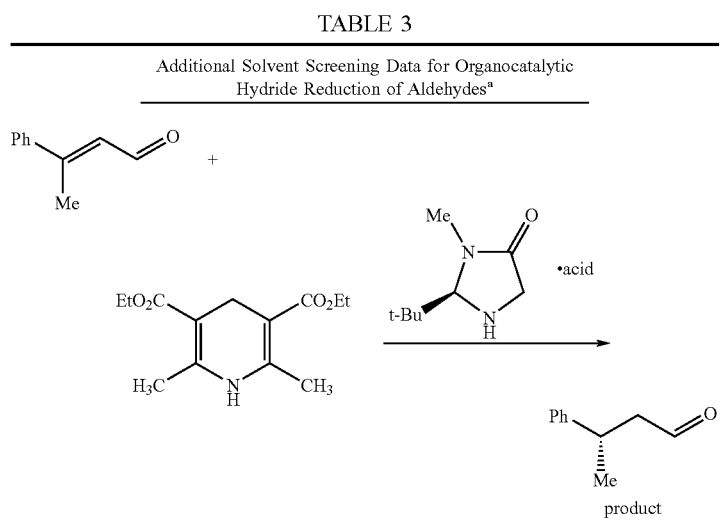

| Entry | Solvent | Acid | Temp [° C.] | Time [h] | Conv. [%] | ee [%] |
|---|---|---|---|---|---|---|
| 1 | MeCN | TFA | 4 | 3 | 48 | 78 |
| 2 | Methanol | TFA | 4 | 3 | 37 | 81 |
| 3 | Hexane | TFA | 4 | 6.5 | 27 | 79 |
| 4 | Tetrahydrofuran | TFA | 4 | 1 | 54 | 87 |

TABLE 3-continued

| | | | | | | |
|---|---|---|---|---|---|---|
| 5 | Et$_2$O | TFA | 4 | 1 | 39 | 86 |
| 6 | CH$_2$Cl$_2$ | TFA | 4 | 1 | 85 | 83 |
| 7 | Toluene | TFA | 4 | 6.5 | 85 | 89 |
| 8 | Acetone | TFA | 4 | 3 | 46 | 82 |
| 9 | EtOAc | TFA | 4 | 1 | 44 | 86 |
| 10 | Toluene | TFA | 0 | 6.5 | 85 | 89 |
| 11 | Et$_2$O | TFA | 0 | 1 | 39 | 86 |
| 12 | CH$_2$Cl$_2$ | TFA | 0 | 1 | 95 | 83 |
| 13 | Tetrahydrofuran | TFA | 0 | 1 | 54 | 87 |
| 14 | CHCl$_3$ | TFA | 0 | 1 | 85 | 85 |
| 15 | CHCl$_3$ | di-NO$_2$BA[c] | 0 | 2 | 97 | 83 |
| 16 | CHCl$_3$ | TCA | 0 | 2 | 96 | 85 |
| 17 | CHCl$_3$ | TBA | 0 | 2 | 94 | 84 |
| 18[b] | Hexane | HCl | 4 | 31 | 33 | 57 |
| 19[b] | Toluene | HCl | 4 | 19 | 89 | 86 |
| 20[b] | Tetrahydrofuran | HCl | 4 | 1.5 | 75 | 76 |
| 21[b] | Dimethylformamide | HCl | 4 | 31 | 75 | 71 |
| 22[b] | CH$_2$Cl$_2$ | HCl | 4 | 19 | 78 | 65 |
| 23[b] | Benzene | HCl | 4 | 19 | 96 | 78 |

[a]using 20 mol % catalyst, 0.1 M solvent. For eaction procedures, see Examples 10-16.
[b]Using catalyst 2 (see Example 9).
[c]2,4-dinitrobenzoic acid.

EXAMPLE 18

TABLE 4

Effect of Temperature on Organocatalytic Hydride Reduction of Aldehydes.[a]

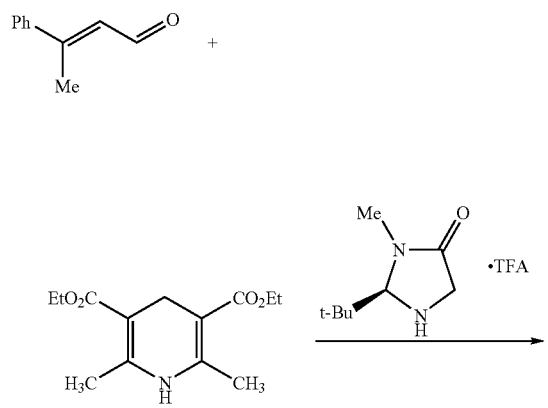

| Entry | Temp [° C.] | Time | Conv. [%] | ee [%] |
|---|---|---|---|---|
| 1 | −10 | 1 | 99 | 89 |
| 2 | −35 | 9 | 92 | 92 |
| 3 | −50 | 24 | 90 | 93 |

[a]using CHCl$_3$ solvent and 20 mol % catalyst. For eaction procedures, see Examples 10-16.

EXAMPLE 19

TABLE 5

Effective of Additives on Organocatalytic Hydride Reduction of Aldehydes.[a]

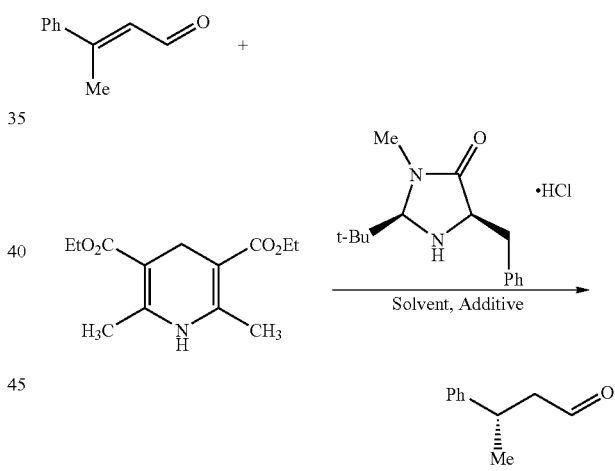

| Entry | Additive | Equivalents of Additive | Time [h] | Conv. [%] | ee [%] |
|---|---|---|---|---|---|
| 1 | None | | <19 | 89 | 86 |
| 2 | H$_2$O | 0.2 | 22 | 84 | 84 |
| 3 | H$_2$O | 1 | 23 | 82 | 82 |
| 4 | MeOH | 0.2 | 23 | 98 | 85 |
| 5 | MeOH | 1 | 23 | 90 | 86 |
| 6 | IPA | 1 | 23 | 91 | 80 |
| 7 | HFIPA | 1 | 10 | 76 | 75 |
| 8 | Phenol | 1 | 10 | 81 | 83 |
| 9 | MeOH | 0.5 | 23 | 83 | 85 |
| 10 | MeOH | 1 | 23 | 99 | 84 |
| 11 | MeOH | 2 | 23 | 84 | 82 |
| 12 | MeOH | 5 | 5 | 83 | 79 |

[1]Reaction at 4° C. and using 20 mol % catalyst, using toluene as solvent.

EXAMPLE 20

TABLE 6

Effect of the Acid Co-catalyst on Organocatalytic Hydride Reduction of Aldehydes.[a]

| Entry | Acid | pKa of acid | Time [h] | Yield [%] | ee [%] |
|---|---|---|---|---|---|
| 1 | TfOH | −14 | 2.5 | 87 | 75 |
| 2 | $HClO_4$ | −10 | 31 | 91 | 76 |
| 3 | p-TSA | −6.5 | 7 | 61 | 90 |
| 4 | HBr | −4.70 | 48 | 36 | 89 |
| 5 | $H_2SO_4$ | −3.0 | 31 | 95 | 86 |
| 6 | $MeSO_3H$ | −2.6 | 31 | 93 | 82 |
| 7 | TFA | 0.23 | 2 | 85 | 89 |
| 8 | TCA | 0.65 | 2.5 | 80 | 87 |
| 9 | TBA | 0.66 | 7 | 64 | 86 |
| 10 | $F_2HCCO_2H$ | 1.24 | 2.5 | 72 | 88 |
| 11 | 2,4-dinitro-benzoic acid | 1.43 | 2 | 50 | 88 |
| 12 | $H_3PO_4$ | 2.12 | 48 | 7 | 86 |
| 13 | $ClH_2CCO_2H$ | 2.86 | 7 | 51 | 87 |
| 14 | AcOH | 3.77 | 48 | 6 | 81 |

[a]At 0° C., using 20 mol % catalyst and toluene as solvent.

EXAMPLE 21

TABLE 7

Effect of Acid Co-catalyst on Organocatalytic Hydride Reduction of Aldehydes: Additional Data[a]

| Entry | Acid | pKa of Acid | Solvent | Conv. [%] | ee [%] |
|---|---|---|---|---|---|
| 1 | HCl | −8 | Toluene | 70 | 81 |
| 2 | HBr | −9 | Toluene | 93 | 82 |
| 3 | HF | 3.7 | Toluene | 98 | 48 |
| 4 | $HNO_3$ | −1.3 | Toluene | 89 | 62 |
| 5 | $MeSO_3H$ | −2.6 | Toluene | 93 | 7 |
| 6 | HBr | −9 | $Et_2O$ | 93 | 82 |
| 7 | HF | 3.7 | $Et_2O$ | 98 | 48 |
| 8 | $HNO_3$ | −1.3 | $Et_2O$ | 89 | 62 |
| 9 | $MeSO_3H$ | −2.6 | $Et_2O$ | 93 | 7 |

[a]At 4° C., using 20 mol % catalyst, 20 mol % acid.

EXAMPLE 22

TABLE 8

Effect of Catalyst on Organocatalytic Hydride Reduction of Aldehydes.[a]

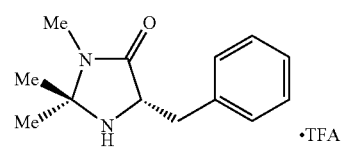

| Entry | Catalyst | Solvent | Time [h] | Conv. [%] | ee [%] |
|---|---|---|---|---|---|
| 1 | No catalyst (Control) | THF | 24 | 0 | 0 |
| 2 | (imidazolidinone·TFA) | THF (23° C.) | 2 | 50 | 55 |

TABLE 8-continued

| # | Catalyst | Solvent | Time (h) | Yield (%) | ee (%) |
|---|---|---|---|---|---|
| 3 | Me-N, t-Bu, 5-benzyl imidazolidinone·TFA | THF (23° C.) | 2 | 60 | 66 |
| 4 | | Toluene | 2 | 82 | 76 |
| 5 | Me-N, t-Bu, 5-(indol-3-ylmethyl) imidazolidinone·TFA | Toluene | 4.5 | 80 | 70 |
| 6 | | Et₂O | | 62 | 63 |
| 7 | n-Bu-N, t-Bu, 5-(N-benzylindol-3-ylmethyl) imidazolidinone·TFA | Toluene | 4.5 | 72 | 66 |
| 8 | | Et₂O | | 54 | 61 |
| 9 | Me-N, adamantyl, 5-benzyl imidazolidinone·TFA | Toluene | 2 | 78 | 75 |
| 10 | | Et₂O | 24 | 64 | 76 |
| 11 | Me-N, t-Bu imidazolidinone·TFA | Toluene | 2 | 85 | 89 |
| 12[b,c] | Me-N, t-Bu imidazolidinone·TFA | Toluene | 1 | 95 | 88 |
| 13[c] | Me-N, t-Bu, 5-benzyl imidazolidinone·TFA | Toluene | 1 | 96 | 75 |
| 14[c] | Me-N, 2,2-diMe, 5-benzyl imidazolidinone·TFA | Toluene | 24 | 37 | 35 |

[a]Unless otherwise specified, reactions at 0° C., using 20 mol % catalyst.
[b]Reaction at 4° C.
[c]Product is the (S) enantiomer.

EXAMPLE 23

TABLE 9

Effect of Hydride Source on Organocatalytic Hydride Reduction of Aldehydes.[a]

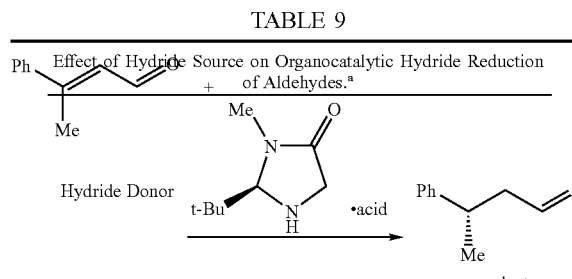

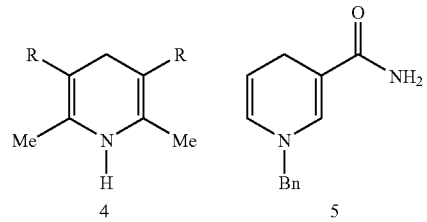

| Entry | Hydride Donor | Time [h] | Conversion [%][b] | ee [%][c] |
|---|---|---|---|---|
| 1 | NADH | 24 | — | — |
| 2 | 5 | 26 | 15 | 88 |

TABLE 9-continued

| | | | | |
|---|---|---|---|---|
| 3 | 4: R = CO$_2$Et | 7 | 92 | 92 |
| 4 | 4: R = CO$_2$Bn | 7 | 94 | 88 |
| 5 | 4: R = CO$_2$Me | 26 | 57 | 89 |
| 6 | 4: R = CO$_2$tBu | 7 | 98 | 94 |
| 7 | 4: R = COPh | 24 | 54 | 80 |
| 8 | 4: R = COMe | 26 | 45 | 86 |

[a]Reaction conditions: 20 mol % catalyst · TCA, CHCl$_3$ −30° C.
[b]Conversion determined by GLC analysis.
[c]Enantiomeric excess determined by chiral GLC analysis (Bodman Γ-TA).

No reaction was observed using NADH (i.e., the hydrogen adduct of Nicotinamide Adenine Dinucleotide) as the hydrogen source.

EXAMPLE 24

TABLE 10

Organocatalytic Hydride Reduction of Aldehydes: Additional Exemplary Reactions.[a]

| Entry | E:Z of Reactant | Product | Hydride Donor | Time [h] | Temp [° C.] | Conv. [%] | ee [%] |
|---|---|---|---|---|---|---|---|
| 1 | >20:1 | BnO-C(O)-CH(Me)-CH$_2$-CHO | R = CO$_2$Et | 24 | −50 | 80 | 87 |
| 2 | >20:1 | BnO-CH$_2$-CH(Me)-CH$_2$-CHO | R = CO$_2$Et | 24 | −30 | 79 | 71 |
| 3 | >20:1 | Me$_2$CH-CH$_2$-CH(Et)-CH$_2$-CHO | R = CO$_2$Et | 22 | −40 | 80 | 41 |
| 4 | >20:1 | Ph-CH(CH(Me)$_2$)-CH$_2$-CHO | R = CO$_2$Et | — | — | 0 | 0 |
| 5 | >20:1 | Me$_2$C=CH-CH$_2$-CH$_2$-CH(Me)-CH$_2$-CHO | R = CO$_2$Et | 7 | | 90 | 37 |
| 6 | | | | 39 | −50 | 92 | 38 |
| 7 | | | R = CO$_2$C(CH$_3$)$_3$ | 1 | −30 | 90 | 62 |
| 8 | | | | 7 | −60 | 90 | 78 |
| 9 | | | | 11 | −70 | 90 | 84 |

TABLE 10-continued

| # | ratio | substrate | R | time | temp | % | ee |
|---|---|---|---|---|---|---|---|
| 7 | >20:1 | Ph-CH(Me)-CH2-CHO (Me,Me) | R = CO$_2$Et | — | — | 0 | 0 |
| 8 | >20:1 | 3-thienyl-CH(Me)-CH2-CHO | R = CO$_2$Et | 60 | −50 | 87 | 79 |
| 9 | 1:1 | Me$_2$CH-CH2-CH(CH2Me)-CH2-CHO | R = CO$_2$Et | 22 | −40 | 100 | 36 |
| 10 | >20:1 | BnO-CH2-CH(Me)-CH2-CHO | R = CO$_2$Et | 24 | −30 | 79 | 71 |
| 11 |  |  |  | 96 | −50 | 67 | 77 |
| 12 | >20:1 | Ph-CH(Me)-CH2-CHO | R = CO$_2$C(CH$_3$)$_3$ | 3 min | RT | 90 | 85 |
| 13 |  |  |  | 0.25 | 0 | 90 | 89 |
| 14 |  |  |  | 7 | −30 | 90 | 95 |
| 15 | 4.6:1 | Cy-CH(Et)-CH2-CHO | R = CO$_2$C(CH$_3$)$_3$ | 8 min | RT | 90 | 81 |
| 16 |  |  |  | 1 | −30 | 90 | 81 |
| 17 |  |  |  | 22 | −60 | 90 | 81 |
| 18 | 13.5:1 |  |  | 0.25 | RT | 90 | 84 |
| 19 |  |  |  | 23 min | 0 | 90 | 86 |
| 20 | — | Ph-CD-CH2-CHO | R = CO$_2$Et | 81 | −50 | 70 | 72 | aReactions using 20 mol % TFA salt of (S)-2-tert-butyl-3-methylimidazolidin-4-one as catalyst.

EXAMPLE 25

General Procedure for the Preparation of Cyclic Ketone Starting Materials

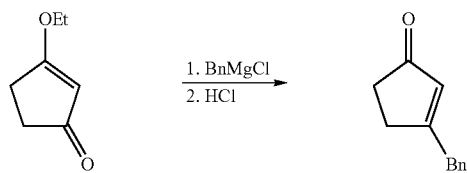

3-benzylcyclopent-2-enone: To a −78° C. solution of benzyl magnesium chloride (14.3 mL, 28.5 mmol, 1.2 eq, 2 M solution in THF) in ether (50 mL) was slowly added 3-ethoxycyclopent-2-enone (2.84 mL, 23.8 mmol, 1 eq.). The reaction mixture was warmed up to −30° C. over 1 hour. At this point, a 1 M solution of HCl was added to the reaction mixture until the pH was adjusted to 1 as indicated by litmus paper. The solution was warmed up to room temperature and the layers were separated. The aqueous phase was extracted with 40 mL of Et$_2$O (3×) and the combined organic layers were washed with 100 mL of brine (1×), dried over anhydrous MgSO$_4$ and concentrated in vacuo. The residual oil was purified by flash chromatography (25% EtOAc/hexanes) to give (3.1 g, 76% yield) of the title compound as a colorless oil.

(Z)-1-butylcyclohept-2-enol: To a clear solution of 2-cyclohepten-1-one (5 g, 45.5 mmol) in ether (50 mL), cooled to 0° C., was added n-BuLi (2.0 M in hexanes, 25 mL, 50.0 mmol) dropwise to produce an opaque yellow solution. The reaction stirred for 2 h at 0° C. and then warmed to room temperature. After 1 h, the reaction was complete as determined by TLC, and quenched in 50 mL NH$_4$Cl. The organic layer was separated and the aqueous layer was extracted with 50 mL of ether (3×). The combined organic layers were dried over Na$_2$SO$_4$, filtered and concentrated in vacuo. The resulting residue was purified by flash chromatography (10% Et$_2$O/pentane) to afford the title compound as a light yellow oil (2 g, 26% yield). IR (film) 3377, 3015, 2930, 2860, 1456, 1378, 1335, 1223, 1121, 1103, 1043, 997 cm$^{-1}$; $^1$H NMR (300 MHz, CDCl$_3$) δ 5.69 (tt, 1H, J=5.6, 11.9 Hz, CCH=CH), 5.59 (d, 1H, J=11.9 Hz, CCH=CH), 2.17-2.09 (m, 2H), 1.84-1.45 (m, 9H), 1.38-1.27 (m, 4H), 0.93-0.88 (m, 3H); $^{13}$C NMR (75 MHz, CDCl$_3$) δ 139.1, 130.0, 76.1, 41.1, 38.5, 27.6, 27.5, 25.6, 24.1, 23.2, 14.1; HRMS (EI$^+$) exact mass calculated for [M]$^+$ (C$_{11}$H$_{20}$O) requires m/z 168.1514, found m/z 168.1516.

(Z)-3-butylcyclohept-2-enone: To a solution of (Z)-1-butylcyclohept-2-enol (2 g, 11.9 mmol) dissolved in dichloromethane (60 mL) was pyridine chlorochromate on basic alumina (20 wt. %, 25.7 g, 23.8 mmol). The resulting reddish solution was stirred at room temperature for 2 h until determined to be complete by TLC. The mixture was diluted in 100 mL diethyl ether and stirred for 1 h after which it was poured over filter paper that was subsequently washed with the ether. The filtrate was partially concentrated (30 mL) and passed through a Florisil column with ether (100 mL). The resulting colorless solution was concentrated and purified by flash chromatography (5% Et$_2$O/Pentane) to provide a colorless oil (920 mg, 47% yield). IR (film) 3477, 2933, 2864, 1662, 1458, 1421, 1375, 1344, 1322, 1267, 1201, 1124, 1103, 1048, 937, 875, 855 cm$^{-1}$; $^1$H NMR (300 MHz, CDCl$_3$) δ 5.89 (s, 1H, COCH), 2.58-2.53 (m, 2H, COCH$_2$), 2.41-2.38 (m, 2H, HC=CCH$_2$), 2.18 (t, 2H, J=6.91 Hz, HC=CCH$_2$(CH$_2$)$_2$CH$_3$), 1.80-1.74 (m, 2H, COCH$_2$CH$_2$), 1.50-1.40 (m, 2H, HC=CCH$_2$CH$_2$), 1.38-1.25 (m, 4H, HC=C(CH$_2$)$_2$CH$_2$CH$_3$), 0.90 (t, 3H, J=7.18 Hz, CH$_2$CH$_3$); $^{13}$C NMR (75 MHz, CDCl$_3$) δ 204.4, 162.4, 128.2, 42.1, 40.8, 32.5, 29.7, 25.1, 22.4, 21.2, 13.9; HRMS (EI$^+$) exact mass calculated for [M]$^+$ (C$_{11}$H$_{18}$O) requires m/z 166.1358, found m/z 166.1359.

Examples 26-37

General Procedure for the Enantioselective Hydrogenation of Cyclic Enones

Procedure A:

To a room temperature solution of 3-substituted-cyclopent-2-enone (1 mmol) and (2S,5S)-5-benzyl-3-methyl-2-(5-methylfuran-2-yl)imidazolidin-4-one (54 mg, 0.2 mmol, 0.2 eq.) dissolved in 1 mL of diethyl ether (1 M) was added trichloroacetic acid (33 mg, 0.2 mmol, 0.2 eq.), and Hantzsch ethyl ester (304 mg, 1.2 mmol, 1.2 eq.). The resulting yellow suspension was stirred at room temperature until the reaction was judged to be complete by TLC. The reaction mixture was passed though a short pad of silica gel and eluted with ether. The resulting solution was concentrated in vacuo and purified by flash chromatography (solvent noted) to provide the title compound.

Procedure B:

To a room temperature solution of 3-substituted-cyclopent-2-enone (1 mmol) and (2S,5S)-5-benzyl-3-methyl-2-(5-methylfuran-2-yl)imidazolidin-4-one (54 mg, 0.2 mmol, 0.2 eq.), dissolved in 1 mL of diethyl ether (1 M) then cooled to 0° C. in an ice bath, was added trichloroacetic acid (33 mg, 0.2 mmol, 0.2 eq.), and Hantzsch t-butyl ester (340 mg, 1.1 mmol, 1.1 eq.). The resulting yellow suspension was stirred at room temperature until the reaction was judged to be complete by TLC. The reaction mixture was passed though a short pad of silica gel with the aid of ether. The resulting solution was concentrated in vacuo and purified by flash chromatography (solvent noted) to provide the title compound.

In noted cases, the resulting pyridine contaminated product was removed post-column by washing with 6 M HCl (2×10 mL), water (1×20 mL), then saturated NaHCO$_3$ (1×20 mL), followed by drying of the organic layer over Na$_2$SO$_4$, filtering and concentrating to afford the title product.

EXAMPLE 26

(R)-3-methylcyclopentanone: Prepared according to the general procedure from 3-methylcyclopent-2-enone (20 mg, 0.204 mmol) for 26 h to provide the title compound (77% conversion, 95% ee). Conversion was determined via GLC analysis by comparison with an internal standard (BnOMe). The physical data were identical in all respects to those of the commercially available (R)-3-methylcyclopentanone. The enantiomeric ratio was determined by GLC using a Bodman Chiraldex Γ-TA (30 m×0.25 mm) column (100° C. isotherm, 1 mL/min.); (S) isomer t$_r$=25.1 min. and (R) isomer t$_r$=25.8 min.

EXAMPLE 27

(R)-3-cyclohexylcyclopentanone: Prepared according to the general procedure from 3-cyclohexylcyclopent-2-enone (164 mg, 1 mmol) for 23 h to provide the title compound as a yellow oil (152 mg, 93% yield, 96% ee) after purification by flash chromatography on Iatrobeads® (15-20% Et$_2$O/pentane). The physical data were identical in all respects to those previously reported (Jones et al. (1998), *Tetrahedron* 54:1471 (racemic product, no optical rotation)). The enantiomeric ratio was determined by GLC using a Hydrodex-B-TBDAc (50 m×0.25 mm) column (105° C. isotherm, 1 mL/min.); (S) isomer t$_r$=127.7 min. and (R) isomer t$_r$=127.9 min. [α]$_D^{22}$=+8.6° (c=1.00, CHCl$_3$).

EXAMPLE 28

(R)-3-tert-butylcyclopentanone: Prepared according to the general procedure from 3-tert-butylcyclopent-2-enone (138 mg, 1 mmol) for 8 h to provide the title compound as a colorless oil (126 mg, 85% yield, 96% ee) after purification by flash chromatography on Iatrobeads® (20% Et$_2$O/pentane). The physical data were identical in all respects to those previously reported (Ahlbrecht (1992), *Synthesis* 1019 (racemic product, no optical rotation)). The enantiomeric ratio was determined by GLC using a Bodman Chiraldex Γ-TA (30 m×0.25 mm) column (90° C. isotherm, 1 mL/min.); (S) isomer t$_r$=14.4 min. and (R) isomer t$_r$=15.0 min. [α]$_D^{22}$=+150.3° (c=1.00, CHCl$_3$).

EXAMPLE 29

(R)-3-benzylcyclopentanone: Prepared according to the general procedure from 3-benzylcyclopent-2-enone (172 mg, 1 mmol) for 24 h at 0° C. After the reaction mixture was passed though a short pad of silica gel, the resulting mixture was poured into 5 mL of a 10% HCl solution and diluted with 5 mL of Et$_2$O. The organic layer was washed with 5 mL of a 10% HCl solution (4×) and with 5 mL of water (1×). The resulting solution was dried over MgSO$_4$ and concentrated in vacuo to provide the title compound as a colorless oil (158 mg, 91% yield, 90% ee) after purification by flash chromatography on Iatrobeads® (2% Et$_2$O/benzene). The physical data were identical in all respects to those previously reported (Yanagisawa et al. (1994), *J. Am. Chem. Soc.* 116:6130; and Moritani et al. (2000), *J. Am. Chem. Soc.* 122:6797 (reported an optical rotation of −96° for the (S)

isomer that is 96% ee)). The enantiomeric ratio was determined by GLC using a Hydrodex-B-TBDAc (50 m×0.25 mm) column (145° C. isotherm, 1 mL/min.); (S) isomer $t_r$=91.5 min. and (R) isomer $t_r$=90.1 min. $[\alpha]_D^2$=+83.9 (c=1.00, CHCl$_3$).

EXAMPLE 30

(R)-3-(benzyloxymethyl)cyclopentanone: Prepared according to the general procedure from 3-(benzyloxymethyl)cyclopent-2-enone (202 mg, 1 mmol) for 24 h at 0° C. After the reaction mixture was passed though a short pad of silica gel, the resulting solution was poured into 5 mL of a 10% HCl solution and diluted with 5 mL of Et$_2$O. The organic layer was washed with 5 mL of a 10% HCl solution (4×) and with 5 mL of water (1×). The resulting solution was dried over MgSO$_4$ and concentrated in vacuo to provide the title compound as a colorless oil (155 mg, 76% yield, 91% ee) after purification by flash chromatography on silica gel (15% Et$_2$O/pentane). The enantiomeric ratio was determined by GLC using a Hydrodex-B-TBDAc (50 m×0.25 mm) column (150° C. isotherm, 1 mL/min.); (S) isomer $t_r$=151.2 min. and (R) isomer $t_r$=153.2 min. IR (film) 3030, 2860, 1740, 1404, 1100 cm$^{-1}$; $^1$H NMR (300 MHz, CDCl$_3$) δ 7.42-7.28 (m, 5H), 4.55 (s, 2H), 3.51 (d, 2H, J=6.3 Hz), 2.61-2.49 (m, 1H), 2.44-2.25 (m, 2H), 2.23-2.01 (m, 3H), 1.84-1.71 (m, 1H); $^{13}$C NMR (75 MHz, CDCl$_3$) δ 219.2, 138.1, 128.3, 127.4, 126.8, 73.2, 73.0, 41.9, 37.8, 36.7, 26.0; HRMS (EI$^+$) exact mass calculated for [M]$^+$ (C$_{13}$H$_{16}$O$_2$) requires m/z 204.1150, found m/z 204.1144; $[\alpha]_D^{22}$=+31.2° (c=1.0, CHCl$_3$).

EXAMPLE 31

(R)-3-phenylcyclopentanone: Prepared according to the general procedure from 3-phenylcyclopent-2-enone (158 mg, 1 mmol) for 8.5 h to provide the title compound as a light yellow oil (140 mg, 89% yield, 74% ee) after purification by flash chromatography on Iatrobeads® (0-2% Et$_2$O/benzene). The physical data were identical in all respects to those previously reported (Gadwood et al. (1987), *J. Org. Chem.* 52:774; Gomez-Bengoa et al. (1998), *J. Am. Chem. Soc.* 120:7649; and Hashimoto et al. (1994), *Synlett.* 353) The enantiomeric ratio was determined by GLC using a Hydrodex-B-TBDAc (50 m×0.25 mm) column (145° C. isotherm, 1 mL/min.); (S) isomer $t_r$=56.3 min. and (R) isomer $t_r$=61.3 min. $[\alpha]_D^{22}$=+60.2° (c=1.00, CHCl$_3$).

EXAMPLE 32

(R)-methyl 3-oxocyclopentanecarboxylate: Prepared according to the general procedure from methyl 3-oxocyclopent-1-enecarboxylate (140 mg, 1 mmol) for 24 h at 0° C. to provide the title compound as a colorless oil (108 mg, 76% yield, 90% ee) after purification by flash chromatography on silica gel (40% Et$_2$O/pentane). The physical data were identical in all respects to those previously reported (Ranu et al. (2001), *Org. Lett.* 3:2603. The absolute stereochemistry was assigned by analogy). The enantiomeric ratio was determined by GLC using a Hydrodex-B-TBDAc (50 m×0.25 mm) column (130° C. isotherm, 1 mL/min.); (S) isomer $t_r$=41.9 min. and (R) isomer $t_r$=43.5 min. $[\alpha]_D^2$=+28.0° (c=1.00, CHCl$_3$).

EXAMPLE 33

(R)-3-acetylcyclopentanone: Prepared according to the general procedure from 3-acetylcyclopent-2-enone (124 mg, 1 mmol) for 24 h at 0° C. to provide the title compound as a colorless oil (103 mg, 82% yield, 93% ee) after purification by flash chromatography on silica gel (50% Et$_2$O/benzene). The physical data were identical in all respects to those previously reported (Monte et al. (1983), *J. Org. Chem.* 48:803 (racemic product, no optical rotation)) enantiomeric ratio was determined by GLC using a Hydrodex-B-TBDAc (50 m×0.25 mm) column (145° C. isotherm, 1 mL/min.); (S) isomer $t_r$=52.0 min. and (R) isomer $t_r$=53.3 min. $[\alpha]_D^{22}$=+56.3° (c=1.0, CHCl$_3$).

EXAMPLE 34

(R)-3-butylcyclohexanone: Prepared according to the general procedure from 3-butylcyclohexen-2-one (168 mg, 1.09 mmol) in 0.2 M Et$_2$O for 43 h at room temperature to provide the title compound as a colorless oil (128.3 mg, 75% yield, 88% ee) after purification by flash chromatography on silica gel (5% Et$_2$O/pentane). The physical data were identical in all respects to those previously reported (Jones et al. (1998). *Tetrahedron* 54:1471; and Moritani et al. (2000), *J. Am. Chem. Soc.* 122:6797 (reported a rotation of −17° for the (S)-enantiomer that is 87% ee)). The enantiomeric ratio was determined by GLC using a Hydrodex-B-TBDAc (50 m×0.25 mm) column (150° C. isotherm, 1 mL/min.); (S) isomer $t_r$=37.0 min. and (R) isomer $t_r$=36.0 min. $[\alpha]_D^{22}$=+15.5° (c=1.00, CHCl$_3$).

EXAMPLE 35

(R)-3-cyclohexylcyclohexanone: Prepared according to the general procedure from 3-cyclohexylcyclohexen-2-one (178 mg, 1.09 mmol) in 0.2 M Et$_2$O for 43 h at room temperature to provide the title compound as a colorless oil (157 mg, 80% yield, 90% ee) after purification by flash chromatography on silica gel (5% Et$_2$O/pentane). The enantiomeric ratio was determined by GLC using a Hydrodex-B-TBDAc (50 m×0.25 mm) column (110° C. isotherm, 1 mL/min.); (S) isomer $t_r$=73.5 min. and (R) isomer $t_r$=65.2 min. IR (film) 2924, 2853, 1715, 1449, 14223, 1346, 1317, 1263, 1225, 1101, 1056, 982, 892, 866 cm$^{-1}$; $^1$H NMR (300 MHz, CDCl$_3$) δ 2.44-2.21 (m, 3H), 2.16-2.04 (m, 2H), 1.93-1.85 (m, 1H), 1.80-1.54 ((m, 8H), 1.47-1.33 (m, 1H), 1.32-1.11 (m, 3H), 1.08-0.92 (m, 2H); $^{13}$C NMR (75 MHz, CDCl$_3$) δ 212.9, 45.6, 44.7, 42.7, 41.6, 30.0, 29.9, 28.4, 26.6, 26.59, 25.54, 25.6; HRMS (EI$^+$) exact mass calculated for [M]$^+$ (C$_{12}$H$_{20}$O) requires m/z 180.1514, found m/z 180.1508; $[\alpha]_D^{22}$+11.9° (c=1.05, CHCl$_3$).

EXAMPLE 36

(R)-3,3,5-trimethylcyclohexanone: Prepared according to the general procedure from isophorone (138 mg, 1.09 mmol) in 0.2 M Et$_2$O for 48 h at room temperature to provide the title compound as a colorless oil (100 mg, 65% yield, 97% ee) after purification by flash chromatography on silica gel (5% Et$_2$O/pentane). The physical data were identical in all respects to those previously reported (Allinger et al. (1975), *J. Org. Chem.* 40:1316 (reported a rotation of +20.3° for the (S)-enantiomer that is 75% ee)). The enantiomeric ratio was determined by GLC using a Hydrodex-B-TBDAc (50 m×0.25 mm) column (110° C. isotherm, 1 mL/min.); (S) isomer $t_r$=11.8 min. and (R) isomer $t_r$=12.4 min. $[\alpha]_D^{22}$=−18.7°(c=1.03, CHCl$_3$).

EXAMPLE 37

(R)-3-butylcycloheptanone: Prepared according to the general procedure from 3-butylcyclohept-2-enone (166.3 mg, 1 mmol) for 48 h at room temperature to provide the title compound as a light yellow oil (106 mg, 63% yield, 82% ee) after purification by flash chromatography on silica gel (5% Et$_2$O/pentane). The physical data were identical in all respects to those previously reported (Strangeland et al. (1997), *Tetrahedron* 53:6503 (reported a rotation of +31.4° for a product that is 92% ee)). The enantiomeric ratio was determined by GLC using a Hydrodex-B-TBDAc (50 m×0.25 mm) column (105° C. isotherm, 1 mL/min.); (S) isomer t$_r$=100.6 min. and (R) isomer t$_r$=102.7 min. $[\alpha]_D^{22}$=+40.3° (c=1.05, CHCl$_3$).

EXAMPLE 38

TABLE 11

Solvent effect on Organocatalytic Hydride Addition of Cyclic Ketones.[a]

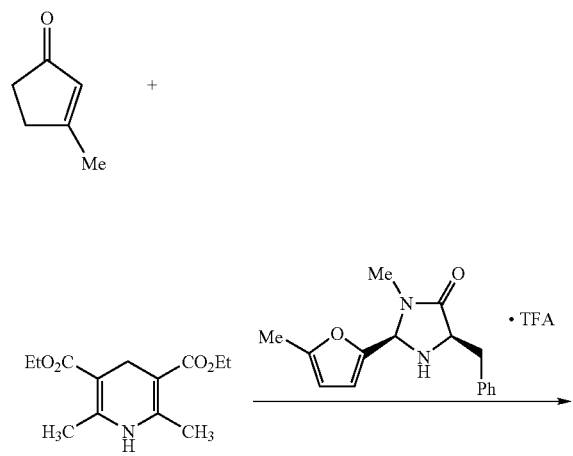

| Entry | Solvent | Dielectric Constant (ε)[b] | Yield [%] | ee [%] |
|---|---|---|---|---|
| 1 | Toluene | 2.38[c] | 91 | 91 |
| 2 | Et$_2$O | 4.34 | 100 | 92 |
| 3 | CHCl$_3$ | 4.8 | 19 | 90 |
| 4 | EtOAc | 6.02[c] | 82 | 89 |
| 5 | THF | 7.58 | 40 | 91 |
| 6 | CH$_2$Cl$_2$ | 8.9 | 37 | 88 |
| 7 | Acetone | 20.7[c] | 80 | 70 |
| 8 | Methanol | 32.6[c] | 63 | 33 |
| 9 | DMF | 37 | 0 | 0 |
| 10 | CH$_3$CN | 37.5 | 18 | 41 |

[a]Reactions at room temperature, 10 h, using 20 mol % catalyst and 1.3 eq. dihydropyridine (relative to ketone).
[b]At 20° C. unless otherwise specified.
[c]At 25° C.

EXAMPLE 39

TABLE 12

Optimization of Co-catalyst in Organocatalytic Hydride Reduction of Cyclic Ketones.[a]

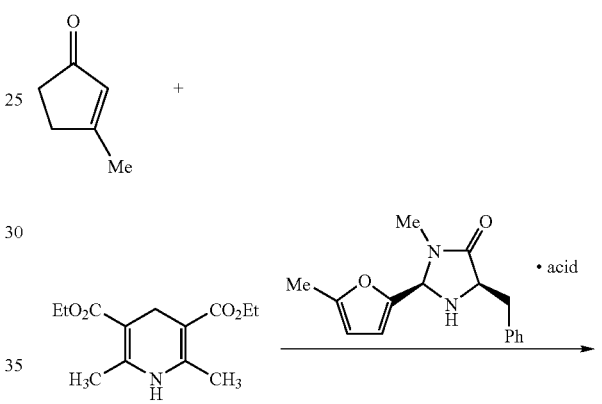

| Entry | Acid | pKa of Acid | Yield [%] | ee [%] |
|---|---|---|---|---|
| 1 | Triflic | −14 | 8 | 72 |
| 2 | HClO$_4$ | −10 | 5 | 57 |
| 3 | HCl | −8.0 | 16 | 78 |
| 4 | p-TSA | ~−6.5 | 9 | 77 |
| 5 | HI | −5.2 | 27 | 86 |
| 6 | HBr | −4.70 | 27 | 78 |
| 7 | H$_2$SO$_4$ | −3.0 | 4 | 64 |
| 8 | MeSO$_3$H | −2.6 | 6 | 62 |
| 9 | TFA | 0.23 | 63 | 63 |
| 10 | TCA | 0.65 | 77 | 77 |
| 11 | TBA | 0.66 | 36 | 36 |
| 12 | DCA | 1.29 | 60 | 60 |
| 13 | di-NO$_2$BA | 1.43 | 59 | 59 |
| 14 | DFA | 1.53 | 45 | 45 |
| 15 | H$_3$PO$_3$ | 2.0 | 6 | 6 |
| 16 | AcOH | 3.77 | 0 | 0 |

[a]Reactions at room temperature, 6 h, using Et$_2$O as solvent, 20 mol % catalyst and 1.3 eq. dihydropyridine (relative to ketone).

EXAMPLE 40

TABLE 13

Screen of Hydride Source in Organocatalytic Hydride Reduction of Cyclic Ketones.[a]

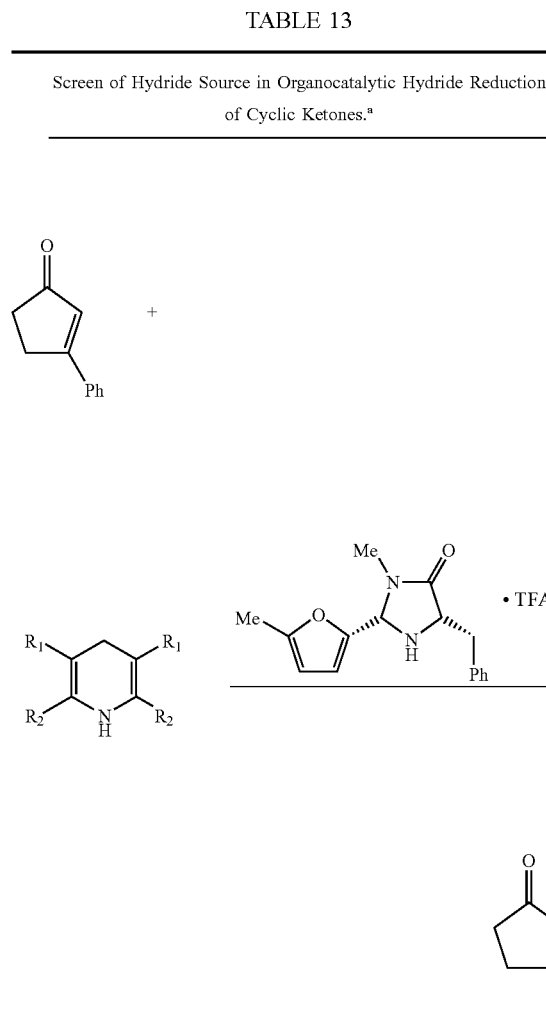

| Entry | Hydride Source | Time [h] | Yield [%] | ee [%] |
|---|---|---|---|---|
| 1 | $R_1$ = CO$_2$Me<br>$R_2$ = i-Pr | 24 | 57 | 86 |
| 2 | $R_1$ = CO$_2$t-Bu<br>$R_2$ = Me | 6 | 86 | 91 |
| 3 | $R_1$ = CO$_2$i-Pr<br>$R_2$ = Me | 3 | 78 | 78 |
| 4 | $R_1$ = CO$_2$Et<br>$R_2$ = Et | 4 | 76 | 82 |
| 5 | $R_1$ = CO$_2$Me<br>$R_2$ = Me | 4 | 76 | 82 |
| 6 | $R_1$ = CO$_2$Et<br>$R_2$ = Me | 3 | 96 | 74 |
| 7 | $R_1$ = CO$_2$Et<br>$R_2$ = H | 3 | 93 | 73 |
| 8 | Acridine | — | 0 | 0 |

[a]Reactions at 0° C., using 1.2 eq. Hydride Source and Et$_2$O as solvent.

EXAMPLE 41

TABLE 14

Example Organocatalytic Hydride Reductions using Cyclic Ketones.[a]

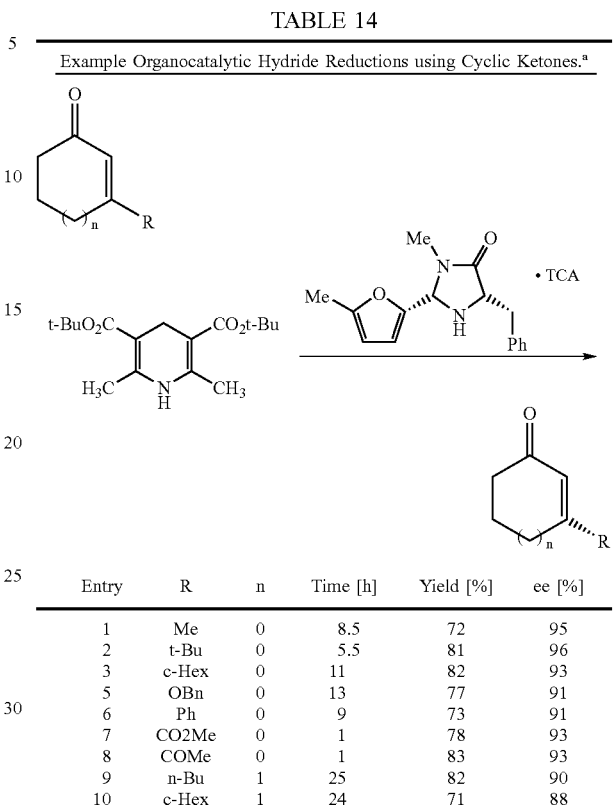

| Entry | R | n | Time [h] | Yield [%] | ee [%] |
|---|---|---|---|---|---|
| 1 | Me | 0 | 8.5 | 72 | 95 |
| 2 | t-Bu | 0 | 5.5 | 81 | 96 |
| 3 | c-Hex | 0 | 11 | 82 | 93 |
| 5 | OBn | 0 | 13 | 77 | 91 |
| 6 | Ph | 0 | 9 | 73 | 91 |
| 7 | CO2Me | 0 | 1 | 78 | 93 |
| 8 | COMe | 0 | 1 | 83 | 93 |
| 9 | n-Bu | 1 | 25 | 82 | 90 |
| 10 | c-Hex | 1 | 24 | 71 | 88 |
| 11 | n-Bu | 2 | 9 | 70 | 92 |

[a]Reactions at 0° C. using Et$_2$O as solvent (0.5 M), 20 mol % catalyst, and 1.1 eq. hydride donor.

EXAMPLE 42

TABLE 15

Example Organocatalytic Hydride Reductions using Cyclic Ketones.[a]

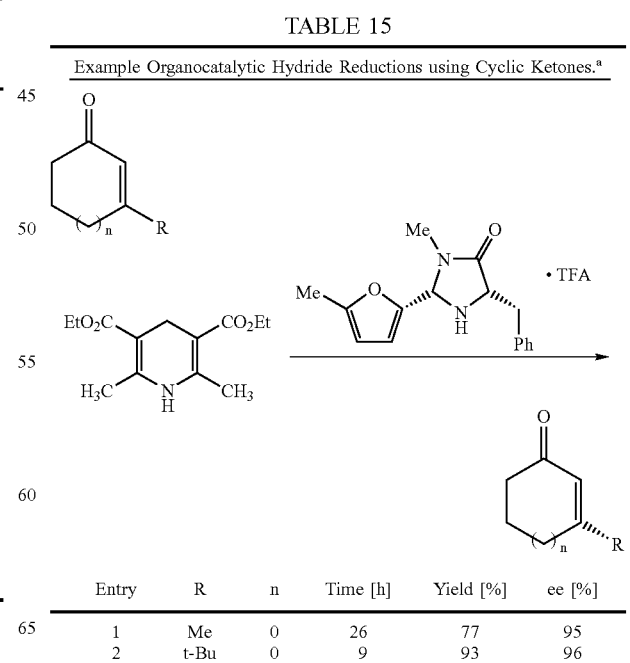

| Entry | R | n | Time [h] | Yield [%] | ee [%] |
|---|---|---|---|---|---|
| 1 | Me | 0 | 26 | 77 | 95 |
| 2 | t-Bu | 0 | 9 | 93 | 96 |

TABLE 15-continued

| | | | | | |
|---|---|---|---|---|---|
| 3 | c-Hex | 0 | 8 | 85 | 96 |
| 4 | OBn | 0 | 24 | 76 | 91 |
| 5 | Ph | 0 | 8.5 | 89 | 74 |
| 6 | CO2Me | 0 | 24 | 76 | 90 |
| 7 | COMe | 0 | 24 | 82 | 93 |
| 8 | n-Bu | 1 | 43 | 75 | 88 |
| 9 | c-Hex | 1 | 43 | 80 | 90 |
| 10 | n-Bu | 2 | 48 | 63 | 82 |

[a] Reactions at 23° C. using $Et_2O$ as solvent (1.0 M) and 20 mol % catalyst.

EXAMPLE 43

TABLE 16

Example Organocatalytic Hydride Reductions using Cyclic Ketones.

| Entry | Substrate | Product | Yield [%] | ee [%] |
|---|---|---|---|---|
| 1[a] | | | 66 | 98 |
| 2[b] | | | 65 | 97 |
| 3 | | | 80 | 50 |
| 4 | | | 67 | ~80 |
| 5 | | | 50 | 90 |
| 6 | | | ~80 | 78 |
| 7 | | | ~80 | 12 |

TABLE 16-continued

Example Organocatalytic Hydride Reductions using Cyclic Ketones.

| Entry | Substrate | Product | Yield [%] | ee [%] |
|---|---|---|---|---|
| 8[a] | | | 78 | 90 |
| 9[b] | | | 91 | 90 |

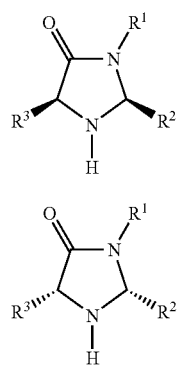

[a]Using conditions from Table 14.
[b]Using conditions from Table 15.

What is claimed is:

1. A process for catalyzing an enantioselective 1,4-hydride reduction of an α,β-unsaturated aldehyde to produce an aldehyde having a chiral carbon at the β-position, wherein the process comprises contacting the α,β-unsaturated aldehyde with a hydride donor in the presence of a catalyst comprising an acid addition salt of an imidazolidinone, wherein the catalyst is capable of lowering the energy level of the lowest unoccupied molecular orbital of the α,β-unsaturated aldehyde and the hydride donor is capable of reacting with the aldehyde by virtue of the lowered LUMO of the compound in the presence of the catalyst, and further wherein the imidazolidinone has the structure of formula (IIA) or (IIB)

(IIA)

(IIB)

wherein:
R[1] is selected from $C_1$-$C_{24}$ hydrocarbyl, substituted $C_1$-$C_{24}$ hydrocarbyl, heteroatom-containing $C_1$-$C_{24}$ hydrocarbyl, and substituted heteroatom-containing $C_1$-$C_{24}$ hydrocarbyl;
R[2] has the structure -$(L)_m$-$CR^4R^5R^6$ wherein m is zero or 1, L is $C_1$-$C_6$ alkylene, and R[4], R[5] and R[6] are $C_1$-$C_{24}$ hydrocarbyl; and
R[3] is selected from H, $C_1$-$C_{24}$ hydrocarbyl, substituted $C_1$-$C_{24}$ hydrocarbyl, heteroatom-containing $C_1$-$C_{24}$ hydrocarbyl, and substituted heteroatom-containing $C_1$-$C_{24}$ hydrocarbyl.

2. The process of claim 1, wherein the acid addition salt is comprised of an acid selected from Brønsted acids, carboxylic acids, and mixtures thereof.

3. The process of claim 1, wherein the hydride donor is a dihydropyridine.

4. The process of claim 3, wherein the hydride donor has the structure of formula (X)

(X)

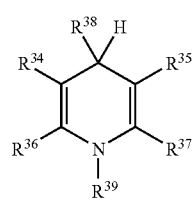

wherein R[34] and R[35] are independently selected from H and deactivating groups, and R[36], R[37], R[38] and R[39] are independently selected from H and activating groups.

5. The process of claim 1, wherein the aldehyde has the structure of formula (VIII)

(VIII)

in which R[29], R[30] and R[31] are independently selected from H, $C_1$-$C_{30}$ hydrocarbyl, heteroatom-containing $C_1$-$C_{30}$ hydrocarbyl, substituted $C_1$-$C_{30}$ hydrocarbyl, substituted heteroatom-containing $C_1$-$C_{30}$ hydrocarbyl, and functional groups, and wherein any two of R[29], R[30] and R[31] can be taken together to form a cycle.

6. The process of claim 5, wherein the α,β-unsaturated aldehyde comprises a mixture of E- and Z-isomers.

7. The process of claim 1, wherein the chiral aldehyde is produced in an enantiomeric excess of at least 85%.

8. A process for catalyzing a 1,4-hydride reduction of an α,β-unsaturated cyclic ketone to produce a ketone product having a chiral carbon at the β-position, wherein the process comprises contacting the α,β-unsaturated cyclic ketone with a dihydropyridine in the presence of a catalyst comprising an acid addition salt of an imidazolidinone, wherein the catalyst is capable of lowering the energy level of the lowest unoccupied molecular orbital of the α,β-unsaturated cyclic ketone and the dihydropyridine is capable of reacting with the ketone by virtue of the lowered LUMO of the compound in the presence of the catalyst.

9. The process of claim 8, wherein the dihydropyridine has the structure of formula (X)

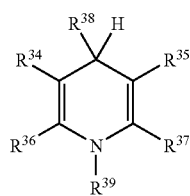

(X)

wherein $R^{34}$ and $R^{35}$ are independently selected from H and deactivating groups, and $R^{36}$, $R^{37}$, $R^{38}$ and $R^{39}$ are independently selected from H and activating groups.

10. The process of claim 8, wherein the imidazolidinone has the structure of formula (VIIA) or (VIIB)

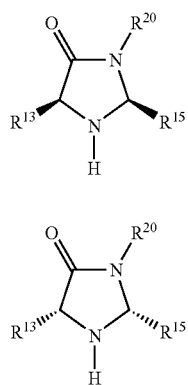

(VIIA)

(VIIB)

wherein:
$R^{20}$ is selected from $C_1$-$C_{24}$ hydrocarbyl, substituted $C_1$-$C_{24}$ hydrocarbyl, heteroatom-containing $C_1$-$C_{24}$ hydrocarbyl, and substituted heteroatoin-containing $C_1$-$C_{24}$ hydrocarbyl;

$R^{13}$ and $R^5$ are independently selected from $C_1$-$C_{24}$ hydrocarbyl, substituted $C_1$-$C_{24}$ hydrocarbyl, heteroatom-containing $C_1$-$C_{24}$ hydrocarbyl, substituted heteroatom-containing $C_1$-$C_{24}$ hydrocarbyl, and functional groups.

11. The process of claim 8, wherein the acid addition salt is comprised of an acid selected from Brønsted acids, carboxylic acids, and mixtures thereof.

12. The process of claim 8, wherein the α,β-unsaturated cyclic ketone has the structure of formula (IX)

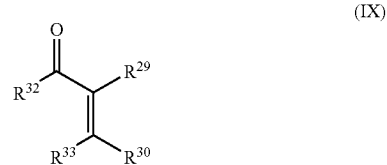

(IX)

wherein:
$R^{29}$, $R^{30}$, $R^{32}$ and $R^{33}$ are independently selected from H, $C_1$-$C_{30}$ hydrocarbyl, heteroatom-containing $C_1$-$C_{30}$ hydrocarbyl, substituted $C_1$-$C_{30}$ hydrocarbyl, substituted heteroatom-containing $C_1$-$C_{30}$ hydrocarbyl, and functional groups;

$R^{32}$ and $R^{33}$ are linked to form a cycle;

any two of $R^{29}$, $R^{30}$ and $R^{32}$ may be linked to form a cycle; and any two of $R^{29}$, $R^{30}$ and $R^{33}$ may be linked to form a cycle.

13. The process of claim 8, wherein the chiral ketone product is produced in an enantiomeric excess of at least 85%.

* * * * *